(12) United States Patent
Jan et al.

(10) Patent No.: US 7,638,667 B2
(45) Date of Patent: Dec. 29, 2009

(54) HYDROCARBON CONVERSION PROCESSES USING A CATALYST COMPRISING A UZM-8HS COMPOSITION

(75) Inventors: Deng-Yang Jan, Elk Grove Village, IL (US); Raelynn M. Miller, LaGrange, IL (US); Mathias P. Koljack, Schaumburg, IL (US); John E. Bauer, LaGrange Park, IL (US); Paula L. Bogdan, Mount Prospect, IL (US); Gregory J. Lewis, Santa Cruz, CA (US); Gregory J. Gajda, Mount Prospect, IL (US); Susan C. Koster, Carpentersville, IL (US); Michael G. Gatter, Elk Grove Village, IL (US); Jaime G. Moscoso, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 379 days.

(21) Appl. No.: 11/457,184

(22) Filed: Jul. 13, 2006

(65) Prior Publication Data
US 2006/0247480 A1    Nov. 2, 2006

Related U.S. Application Data

(63) Continuation-in-part of application No. 10/828,989, filed on Apr. 21, 2004, now Pat. No. 7,091,390, which is a continuation-in-part of application No. 10/395,466, filed on Mar. 21, 2003, now Pat. No. 6,756,030, and a continuation-in-part of application No. 10/395,624, filed on Mar. 21, 2003, now abandoned.

(51) Int. Cl.
*C07C 2/66* (2006.01)

(52) U.S. Cl. .................................................. 585/467
(58) Field of Classification Search ................ 585/467; 423/718
See application file for complete search history.

(56) References Cited

U.S. PATENT DOCUMENTS

| | | | |
|---|---|---|---|
| 4,610,856 A | 9/1986 | Skeels et al. | 423/328 |
| 4,826,667 A | 5/1989 | Zones et al. | 423/277 |
| 5,236,575 A | 8/1993 | Bennett et al. | 208/46 |
| 5,310,715 A | 5/1994 | Kresge et al. | 502/84 |
| 5,362,697 A | 11/1994 | Fung et al. | 502/71 |
| 5,827,491 A | 10/1998 | Emerson et al. | 423/328.2 |
| 6,569,401 B1 | 5/2003 | Elomari | 423/718 |
| 6,613,302 B1 | 9/2003 | Moscoso et al. | 423/718 |
| 6,713,041 B1 | 3/2004 | Moscoso et al. | 423/705 |
| 6,756,030 B1 | 6/2004 | Rohde et al. | 423/718 |
| 2003/0180217 A1 | 9/2003 | Canos et al. | 423/718 |
| 2003/0211034 A1 | 11/2003 | Wilson et al. | 423/713 |

OTHER PUBLICATIONS

D. W. Breck, *Zeolite Molecular Sieves*, Wiley and Sons, New York, (1974), p. 441.
J. Phys. Chem., 1996, 100, p. 3788-3798.

*Primary Examiner*—Thuan Dinh Dang
(74) *Attorney, Agent, or Firm*—Frank S Molinaro

(57) ABSTRACT

Hydrocarbon conversion processes using a new family of zeolites identified as UZM-8HS are described. The UZM-8HS zeolite are derived from UZM-8 zeolites by treating the UZM-8 with a fluoro-silicate salt, an acid, etc. The UZM-8HS zeolites have unique x-ray diffraction patterns. These zeolites can be used in alkylation of aromatics, transalkylation of aromatics, isomerization of aromatics and alkylation of isoparaffins.

8 Claims, 8 Drawing Sheets

HYDROCARBON CONVERSION PROCESSES USING A CATALYST COMPRISING A UZM-8HS COMPOSITION

CROSS-REFERENCE TO RELATED APPLICATIONS

This application is a Continuation-In-Part of application Ser. No. 10/828,989, filed Apr. 21, 2004, which in turn is a Continuation-In-Part of application Ser. No. 10/395,466 filed Mar. 21, 2003, now U.S. Pat. No. 6,756,030 B1 and Ser. No. 10/395,624 filed Mar. 21, 2003, now abandoned, the contents of which are hereby incorporated by reference in their entirety.

FIELD OF THE INVENTION

This invention relates to hydrocarbon conversion processes using an aluminosilicate zeolite designated UZM-8HS. The hydrocarbon conversion processes are selected from transalkylation of aromatics, alkylation of aromatics, isomerization of aromatics and alkylation of isoparaffins.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared, are used in various industrial processes. Synthetic zeolites are prepared, via hydrothermal synthesis employing suitable sources of Si and Al, as well as structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversions, which can take place on outside surfaces as well as on internal surfaces within the pore.

In U.S. Pat. No. 6,756,030 B1, a new family of materials designated UZM-8 is disclosed. The UZM-8 materials are zeolitic aluminosilicates ranging in Si/Al ratio from 6.5 to 35. They are prepared from reaction mixtures employing organoammonium structure directing agents with preferred examples being diethyldimethylammonium (DEDMA), ethyltrimethylammonium (ETMA), and hexamethonium (HM) cations and optionally alkali or alkaline earth metals and/or other organoammonium cations. The UZM-8 materials have a unique x-ray diffraction pattern and a composition on an as synthesized and anhydrous basis expressed by an empirical formula of:

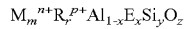

$$M_m^{n+}R_r^{p+}Al_{1-x}E_xSi_yO_z$$

where M is at least one exchangeable cation selected from the group consisting of alkali and alkaline earth metals, "m" is the mole ratio of M to (Al+E) and varies from 0 to about 2.0, R is at least one organoammonium cation selected from the group consisting of quaternary ammonium cations, diquaternary ammonium, protonated amines, protonated diamines, protonated alkanolamines and quaternized alkanolammonium, "r" is the mole ratio of R to (Al+E) and has a value of about 0.05 to about 5.0, "n" is the weighted average valence of M and has a value of about 1 to about 2, "p" is the weighted average valence of R and has a value of about 1 to about 2, E is an element selected from the group consisting of gallium, iron, boron, chromium, indium and mixtures thereof, "x" is the mole fraction of E and has a value from 0 to about 1.0, "y" is the mole ratio of Si to (Al+E) and varies from about 6.5 to about 35 and "z" is the mole ratio of O to (Al+E) and has a value determined by the equation:

$$z=(m \cdot n + r \cdot p + 3 + 4 \cdot y)/2.$$

Applicants have now modified these UZM-8 materials in order to change some of their properties. By using one or more techniques selected from acid extraction, calcination, steaming and ammonium hexafluorosilicate treatment, applicants have been able to control the aluminum content of the UZM-8 zeolites to nearly all silica while maintaining their structure and porosity. Dealumination strategies are known in the art and are given by Breck (see D. W. Breck, *Zeolite Molecular Sieves*, Wiley and Sons, New York, (1974), p. 441) and Skeels and Breck (see U.S. Pat. No. 4,610,856). The result is a modified UZM-8 (UZM-8HS) material containing less aluminum than the starting UZM-8 composition. Control of the Al content in the zeolite allows one to tune the properties associated with the Al, such as ion-exchange capacity and acidity thereby providing improved catalysts and/or adsorbents. This new family of materials is designated UZM-8HS.

Because of the changes in the UZM-8HS compositions, they have been found to be useful in various hydrocarbon conversion processes such as alkylation of aromatic compounds, transalkylation, etc.

SUMMARY OF THE INVENTION

As stated, this invention relates to hydrocarbon processes using UZM-8HS crystalline compositions. Accordingly, one embodiment of the invention is a hydrocarbon conversion process comprising contacting a hydrocarbon stream with a catalytic composite at hydrocarbon conversion conditions to give a converted product, the hydrocarbon conversion processes selected from the group consisting of alkylation of aromatics, transalkylation of aromatics, isomerization of aromatics and alkylation of isoparaffins and the catalytic composite comprising UZM-8HS where UZM-8HS has a three-dimensional framework of at least $AlO_2$ and $SiO_2$ tetrahedral units and an empirical composition on an anhydrous basis in terms of mole ratios of the elements of:

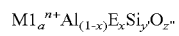

$$M1_a^{n+}Al_{(1-x)}E_xSi_{y'}O_{z''}$$

where M1 is at least one exchangeable cation selected from the group consisting of alkali metals, alkaline earth metals, rare earth metals, ammonium ion, hydrogen ion and mixtures thereof, a is the mole ratio of M1 to (Al+E) and varies from about 0.05 to about 50, E is an element selected from the group consisting of gallium, iron, boron, chromium, indium and mixtures thereof, x is the mole fraction of E and varies from 0 to about 1.0, n is the weighted average valence of M1 and has a value of about +1 to about +3, y' is the mole ratio of Si to (Al+E) and is greater than about 6.5 and z" is the mole ratio of O to (Al+E) and has a value determined by the equation:

$$z''=(a \cdot n + 3 + 4 \cdot y')/2$$

the zeolite characterized in that it has an x-ray diffraction pattern having at least the d-spacings and relative intensities shown in Table B.

TABLE B

UZM-8HS

| 2-θ | d(Å) | I/I$_o$ % |
|---|---|---|
| 6.90-7.40 | 12.8-11.94 | w-vs |
| 8.15-8.66 | 10.84-10.21 | m-vs |
| 14.10-14.70 | 6.28-6.02 | w-vs |
| 19.40-20.10 | 4.57-4.41 | w-s |
| 22.00-22.85 | 4.04-3.89 | m-vs |
| 24.65-25.40 | 3.61-3.50 | w-m |
| 25.70-26.50 | 3.46-3.36 | w-vs |

This and other objects and embodiments will become more apparent after a detailed description of the invention.

DETAILED DESCRIPTION OF THE INVENTION

Figure 1:
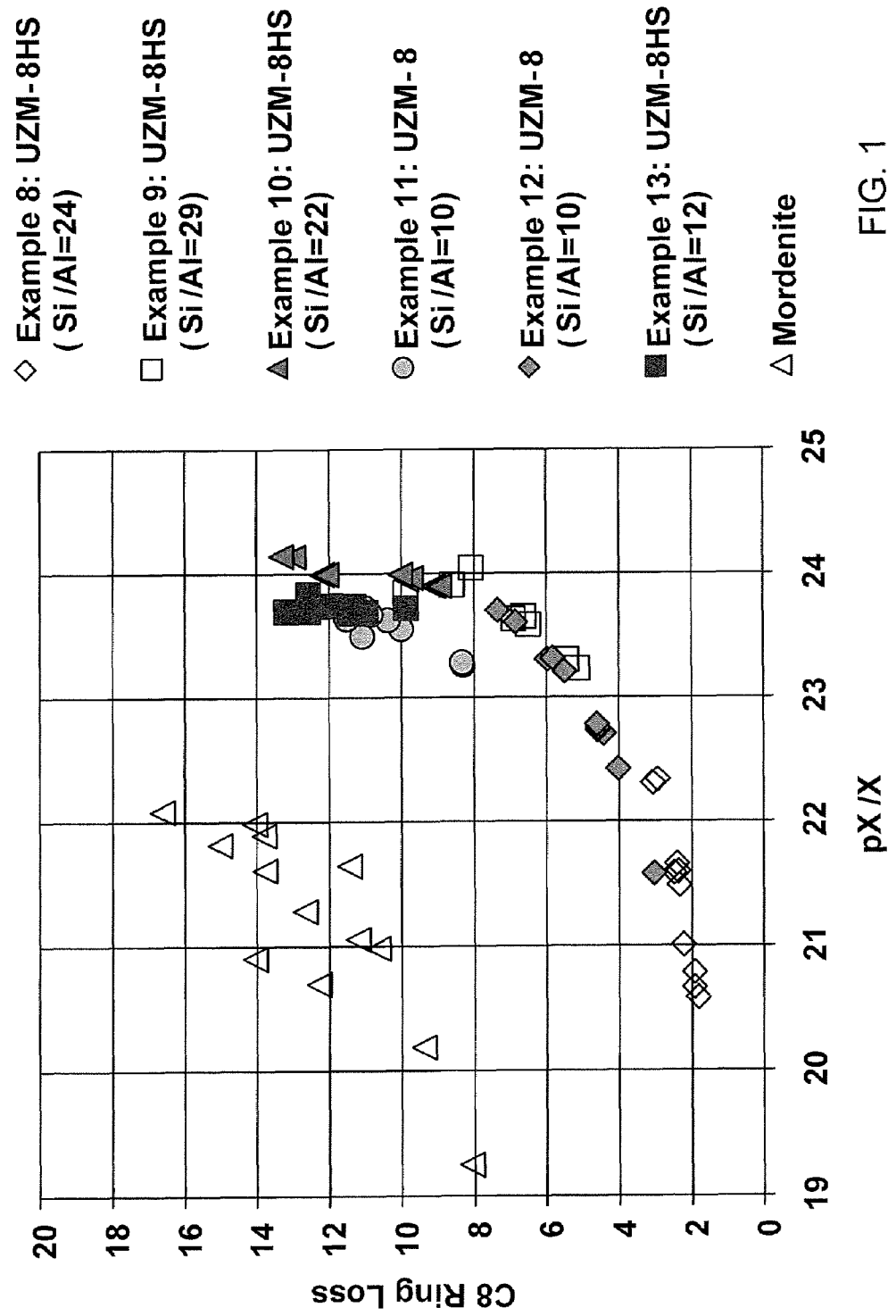
FIG. 1 presents plots of PX/X versus $C_8$ ring loss for catalysts from examples 8 to 13 and mordenite.

The catalytic composition which is used in the processes of the current invention comprises UZM-8HS. UZM-8HS is obtained by treating a starting zeolite having the topology of UZM-8 with: a) a fluorosilicate solution or slurry; b) calcination or steaming followed by acid extraction or ion-exchange; c) acid extraction or d) any combination of these processes in any order. UZM-8 is described in U.S. Pat. No. 6,756,030 B1, the contents of which are incorporated in their entirety by reference. As described in the '030 patent, UZM-8 has a composition in the as-synthesized form on an anhydrous basis expressed by the empirical formula:

$$M_m^{n+}R_r^{p+}Al_{(1-x)}E_xSi_yO_z \quad (1)$$

where M is at least one exchangeable cation and is selected from the group consisting of alkali and alkaline earth metals. Specific examples of the M cations include but are not limited to lithium, sodium, potassium, cesium, strontium, calcium, magnesium, barium and mixtures thereof. The value of m which is the mole ratio of M to (Al+E) varies from 0 to about 2. R is at least one organoammonium cation selected from the group consisting of protonated amines, protonated diamines, protonated alkanolamines, quaternary ammonium ions, diquaternary ammonium ions, quaternized alkanolammonium ions. Preferred organoammonium cations are those that are non-cyclic or those that do not contain a cyclic group as one substituent. Of these, those that contain at least two methyl groups as substituents are especially preferred. Examples of preferred cations include but are not limited to DEDMA, ETMA and HM. The value of r which is the mole ratio of R to (Al+E) varies from about 0.05 to about 5.0. The value of n, which is the weighted average valence of M, varies from +1 to about +2. The value of p, which is the average weighted valence of the organic cation has a value from about +1 to about +2. E is an element which is tetrahedrally coordinated, is present in the framework and is selected from the group consisting of gallium, iron, boron, chromium, indium, and mixtures thereof. The value of x which is the mole fraction of E varies from 0 to about 1.0. The ratio of Si to (Al+E) is represented by y which varies from about 6.5 to about 35, while the mole ratio of O to (Al+E) is represented by z and has a value given by the equation:

$$z=(m\cdot n+r\cdot p+3+4\cdot y)/2.$$

When M is only one metal, then the weighted average valence is the valence of that one metal, i.e. +1 or +2. However, when more than one M metal is present, the total amount of:

$$M_m^{n+}=M_{m1}^{(n1)+}+M_{m2}^{(n2)+}+M_{m3}^{(n3)+}+\ldots$$

and the weighted average valence n is given by the equation:

$$n = \frac{m_1 \cdot n_1 + m_2 \cdot n_2 + m_3 \cdot n_3 + \cdots}{m_1 + m_2 + m_3 \cdots}$$

Similarly when only one R organic cation is present, the weighted average valence is the valence of the single R cation, i.e., +1 or +2. When more than one R cation is present, the total amount of R is given by the equation:

and the weighted average valence p is given by the equation:

$$p = \frac{p_1 \cdot r_1 + p_2 \cdot r_2 + p_3 \cdot r_3 + \cdots}{r_1 + r_2 + r_3 + \cdots}$$

These aluminosilicate zeolites (UZM-8) are prepared by a hydrothermal crystallization of a reaction mixture prepared by combining reactive sources of M, R, aluminum, and silicon in aqueous media. Often these reaction mixtures are homogenous solutions and may be alkali free. Accordingly, the aluminum sources include, but are not limited to, aluminum alkoxides, precipitated alumina, aluminum hydroxide, aluminum salts and aluminum metal. Specific examples of aluminum alkoxides include, but are not limited to aluminum sec-butoxide, and aluminum isopropoxide. Sources of silica include but are not limited to tetraethylorthosilicate, fumed silicas, precipitated silicas and colloidal silica. Sources of the M metals include the halide salts, nitrate salts, acetate salts, and hydroxides of the respective alkali or alkaline earth metals. R can be introduced as an organoammonium cation or as an amine. In the case where R is a quaternary ammonium cation or a quaternized alkanolammonium cation, the sources include but are not limited to the hydroxide, chloride, bromide, iodide and fluoride compounds. Specific examples include without limitation diethyldimethylammonium (DEDMA) hydroxide, ethyltrimethylammonium (ETMA) hydroxide, tetramethylammonium hydroxide, tetraethylammonium hydroxide, hexamethonium bromide, tetramethylammonium chloride, methyltriethylammonium hydroxide and tetramethylammonium carbonate. R may also be introduced as a neutral amine, diamine, and alkanolamine which hydrolyzes to give an organoammonium cation. Specific examples are triethanolamine, triethylamine, and N,N,N',N' tetramethyl-1,6-hexanediamine. Any mixtures of the above mentioned forms of R may also be employed. Preferred sources of R include without limitation ETMAOH, DEDMAOH and HM(OH)$_2$.

The reaction mixture containing reactive sources of the desired components can be described in terms of molar ratios of the oxides by the formula:

$$aM_{2/n}O:bR_{2/n}O:(1-c)Al_2O_3:cE_2O_3:dSiO_2:eH_2O$$

where a is the mole ratio of the oxide of M and has a value of 0 to about 25, b is the mole ratio of the oxide of R and has a value of about 1.5 to about 80, d is the mole ratio of silica and has a value of about 10 to about 100, c is the mole fraction of the oxide of E and has a value from 0 to about 1.0, and e is the mole ratio of water and has a value of about 100 to about 15000. The reaction mixture is now reacted at a temperature of about 85° C. to about 225° C. and preferably from about 120° C. to about 150° C. for a period of about 1 day to about 28 days and preferably for a time of about 5 days to about 14 days in a sealed reaction vessel under autogenous pressure. After crystallization is complete, the solid product is isolated from the heterogeneous mixture by means such as filtration or centrifugation, and then washed with de-ionized water and dried in air at ambient temperature up to about 100° C.

UZM-8 can be identified by its x-ray diffraction pattern having at least the d-spacing and relative intensities set forth in Table A.

TABLE A

| UZM-8 | | |
|---|---|---|
| 2-θ | d(Å) | I/I$_o$ % |
| 6.40-6.90 | 13.80-12.80 | w-s |
| 6.95-7.42 | 12.70-11.90 | m-s |
| 8.33-9.11 | 10.60-9.70 | w-vs |
| 19.62-20.49 | 4.52-4.33 | m-vs |
| 21.93-22.84 | 4.05-3.89 | m-vs |
| 24.71-25.35 | 3.60-3.51 | w-m |
| 25.73-26.35 | 3.46-3.38 | m-vs |

The cation population of the starting UZM-8 is not a critical factor of the instant process insofar as the dealumination processes are concerned, but can have a bearing on the final result, especially with regard to the extent of dealumination. Thus, the UZM-8 can be used as synthesized or can be ion exchanged to provide a different cation form. In this respect, the starting zeolite can be described by the empirical formula:

$$M'_{m'}{}^{n'+}R_{r'}{}^{p+}Al_{(1-x)}E_xSi_yO_{z'} \quad (2)$$

where R, x, y, and E are as described above and m' has a value from 0 to about 7.0, M' is a cation selected from the group consisting of alkali metals, alkaline earth metals, rare earth metals, hydrogen ion, ammonium ion, and mixtures thereof, n' is the weighted average valence of M' and varies from about 1 to about 3, r' has a value from 0 to about 7.0, r'+m'>0, and p is the weighted average valence of R and varies from about +1 to +2. The value of z' is given by the formula:

$$z'=(m'\cdot n'+r'\cdot p+3+4\cdot y)/2.$$

The designation UZM-8 will be used to refer to the zeolite represented by formula (2) which includes both the as-synthesized and ion exchanged forms of the zeolite.

Methods used to exchange one cation for another are well known in the art and involve contacting the microporous compositions with a solution containing the desired cation (at molar excess) at exchange conditions. Exchange conditions include a temperature of about 15° C. to about 100° C. and a time of about 20 minutes to about 50 hours. The organic cation can also be removed prior to ion exchange by heating under controlled conditions. A special case of ion-exchange is ammonia calcination, in which the organic template can be decomposed and replaced by ammonium cation.

In a preferred case, especially for dealumination by treatment with a fluorosilicate solution, the UZM-8 is exchanged with ammonium cation by contacting it with ammonium nitrate at a temperature of 15° C. to about 100° C., followed by a water wash. This procedure may be repeated several times. Finally, the exchanged UZM-8 zeolite is dried at 100° C.

One process of preparing the UZM-8HS of the present invention is by treating the UZM-8 composition described above with a fluorosilicate salt at a temperature of about 20° C. to about 90° C. The fluorosilicate salt serves two purposes. It removes aluminum atoms from the framework and provides a source of extraneous silicon, which can be inserted into the framework (replacing the aluminum). The fluorosilicate salts which can be used are described by the general formula:

$$A_{2/n}SiF_6$$

where n is the valence of A and A is a cation selected from the group consisting of NH$_4^+$, H$^+$, Mg$^{2+}$, Li$^+$, Na$^+$, Ba$^{2+}$, Cd$^{2+}$, Cu$^+$, Cu$^{2+}$, Ca$^{2+}$, Cs$^+$, Fe$^{2+}$, Ca$^{2+}$, Pb$^{2+}$, Mn$^{2+}$, Rb$^+$, Ag$^+$, Sr$^{2+}$, Tl$^+$, and Zn$^{2+}$. The ammonium fluorosilicate is most preferred because of its substantial solubility in water and because it forms water soluble by-product salts upon reaction with the zeolite, namely (NH$_4$)$_3$AlF$_6$.

The fluorosilicate salt is contacted with the UZM-8 zeolite in the form of an aqueous solution or slurry at a pH in the range of about 3 to about 7. This solution is contacted with the zeolite either incrementally or continuously at a slow rate such that a sufficient proportion of the framework aluminum atoms removed are replaced by silicon atoms to retain at least 50%, preferably at least 70% of the framework (crystalline) structure of the starting UZM-8 zeolite. The amount of fluorosilicate necessary to carry out the process of this invention can vary considerably, but should be at least in an amount of 0.0075 moles of the fluorosilicate salt per 100 grams of starting zeolite. Once the reaction is complete, the product zeolite UZM-8HS is isolated by conventional techniques such as filtration.

Without wishing to be bound by any particular theory, the process of removing aluminum and inserting the silicon appears to proceed in two steps in which the aluminum extraction step will, unless controlled, proceed very rapidly while the silicon insertion is relatively slow. If dealumination becomes too extensive without silicon substitution, the crystal structure becomes seriously degraded and ultimately collapses. In general, the rate of aluminum extraction is decreased as the pH of the fluorosilicate solution in contact with the zeolite is increased within the range of about 3 to about 7 and as the concentration of the fluorosilicate in the reaction system is decreased. At pH values below 3, crystal degradation can be unduly severe, whereas at pH values higher than 7, silicon insertion is unduly slow. Also, increasing the reaction temperature tends to increase the rate of substitution of silicon. Increasing the reaction temperature has been found to have less of an effect on dealumination than the pH of the solution. Therefore, the pH may be considered a means of controlling the dealumination while temperature may be considered as a means of controlling the substitution rate.

Theoretically, there is no lower limit for the concentration of fluorosilicate salt in the aqueous solution employed, provided, of course, the pH of the solution is high enough to avoid undue destructive attack on the UZM-8 zeolite structure apart from the intended reaction with the fluorosilicate. A slow rate of addition of fluorosilicate salts insures that adequate time is permitted for the insertion of silicon into the framework before excessive aluminum extraction occurs with consequent collapse of the crystal structure. In general the effective reaction temperature is between about 10° C. and 99° C., preferably between about 20° C. and 95° C., but temperatures of 125° C. or higher and as low as 0° C. can be used.

The maximum concentration of fluorosilicate salt in the aqueous solution employed is, of course, interrelated to the temperature and pH factors and also with the time of contact between the zeolite and the solution and the relative proportions of zeolite and fluorosilicate salt. Solutions having fluorosilicate salt concentrations of between $10^{-3}$ moles per liter of solution and up to saturation of the solution can be employed, but it is preferred that concentrations in the range of between about 0.05 and about 2.0 moles per liter of solution be used. In addition, as hereinbefore discussed, slurries of the fluorosilicate salts may be employed. The aforementioned concentration values are with respect to true solutions, and are not intended to apply to the total fluorosilicate salts in slurries of the salts in water. Even very slightly soluble fluorosilicate salts can be slurried in water and used as a reagent, the undissolved solids being readily available to replace dissolved molecular species consumed in reaction with the zeolite. The minimum value for the amount of fluoro salt to be added is preferably at least equivalent to the minimum mole fraction of aluminum to be removed from the zeolite.

It has been found that when large amounts of silicon atoms are to be substituted, i.e., increasing the $SiO_2/Al_2O_3$ ratio by more than 100%, it is preferable to carry out the process in multiple steps in order to minimize crystal degradation. That is, contacting with the fluorosilicate salt is carried out in two or more steps using a lower concentration of the fluorosilicate salt than required to replace the desired amount of silicon in one step. After each fluorosilicate treatment, the product is washed to remove fluoride and aluminum. Drying of the zeolite at 50° C. between treatments may also be done to facilitate the handling of the wet zeolite product.

Another embodiment of the invention involves contacting the UZM-8 starting zeolite with an acid (acid extraction) in order to remove some of the aluminum from the framework and thereby provide the UZM-8HS zeolite of the invention. Although it is known that aluminum can be extracted from the framework by acids, it is not predictable whether the resulting product will retain a substantial portion of its crystallinity or whether the structure will collapse resulting in an amorphous material. Applicants have discovered that UZM-8 can be dealuminated to nearly pure silica forms while maintaining substantial crystallinity, surface area and micropore volume.

The acids which can be used in carrying out acid extraction include without limitation mineral acids, carboxylic acids and mixtures thereof. Examples of these include sulfuric acid, nitric acid, ethylene diaminetetraacetic acid (EDTA), citric acid, oxalic acid, etc. The concentration of acid which can be used is not critical but is conveniently between about 1 wt. % to about 80 wt. % acid and preferably between 5 wt. % and 40 wt. % acid. Acid extraction conditions include a temperature of about 10° C. to about 100° C. for a time of about 10 minutes to about 24 hours. Once treated with the acid, the UZM-8HS zeolite is isolated by means such as filtration, washed with deionized water and dried at ambient temperature up to about 100° C.

The extent of dealumination obtained from acid extraction depends on the cation form of the starting UZM-8 as well as the acid concentration and the time and temperature over which the extraction is conducted. For example, if organic cations are present in the starting UZM-8, the extent of dealumination will be slight compared to a UZM-8 in which the organic cations have been removed. This may be preferred if it is desired to have dealumination just at the surface of the UZM-8. Convenient ways of removing the organic cations include calcination, ammonia calcination, steaming and ion exchange. Calcination conditions include a temperature of about 300° C. to about 600° C. for a time of about 2 to about 24 hours. Steaming conditions include a temperature of about 400° C. to about 850° C. with from about 1% to about 100% steam for a time of about 10 minutes to about 48 hours and preferably a temperature of about 500° C. to about 600° C., steam concentration of about 5 to about 50% and a time of about 1 to about 2 hours. Ion exchange conditions are as set forth above.

A special treatment for removing organic cations to obtain the ammonium ion exchanged form is ammonia calcination. Calcination in an ammonia atmosphere can decompose organic cations, presumably to a proton form that can be neutralized by ammonia to form the ammonium cation. The stability of the ammonium form of the zeolite prevents dealumination upon hydration, which occurs extensively in lower ratio zeolites in the proton forms obtained in air calcinations. The resulting ammonium form of the zeolite can be further ion-exchanged to any other desired form. Ammonia calcination conditions include treatment in the ammonia atmosphere at temperatures between about 250° C. and about 600° C. and more preferably between about 250° C. and about 450° C. for times of 10 minutes to 5 hours. Optionally, the treatments can be carried out in multiple steps within this temperature range such that the total time in the ammonia atmosphere does not exceed 5 hours. Above 500° C., the treatments should be brief, less than a half hour and more preferably on the order of 5-10 minutes. Extended calcination times above 500° C. can lead to unintended dealumination along with the desired ammonium ion-exchange and are unnecessarily harsh as most organoammonium templates easily decompose at lower temperatures.

It should be pointed out that both calcination and steaming treatments not only remove organic cations, but can also dealuminate the zeolite. Thus, alternate embodiments of the invention include: a calcination treatment followed by acid extraction and steaming followed by acid extraction. A further embodiment of the invention comprises calcining or steaming the starting UZM-8 zeolite followed by an ion-exchange treatment. Of course an acid extraction can be carried out concurrently with, before or after the ion exchange.

The ion exchange conditions are the same as set forth above, namely a temperature of about 15° C. to about 100° C. and a time of about 20 minutes to about 50 hours. Ion exchange can be carried out with a solution comprising a cation (M1') selected from the group consisting of alkali metals, alkaline earth metals, rare earth metals, hydrogen ion, ammonium ion, and mixtures thereof. By carrying out this ion exchange, the M1 cation is exchanged for a secondary or different M1' cation. In a preferred embodiment, the UZM-8HS composition after the steaming or calcining steps is contacted with an ion exchange solution comprising an ammonium salt. Examples of ammonium salts include but are not limited to ammonium nitrate, ammonium chloride, ammonium bromide, and ammonium acetate. The ammonium ion containing solution can optionally contain a mineral acid such as but not limited to nitric, hydrochloric, sulfuric and mixtures thereof. The concentration of the mineral acid is that amount necessary to give a ratio of $H^+$ to $NH_4^+$ of 0 to 1. This ammonium ion exchange aids in removing any debris present in the pores after the steaming and/or calcination treatments.

It is apparent from the foregoing that, with respect to effective process conditions, it is desirable that the integrity of the zeolite crystal structure be substantially maintained throughout the dealumination process, and that the zeolite retains at least 50%, preferably at least 70 and more preferably at least 90% of its original crystallinity. A convenient technique for assessing the crystallinity of the products relative to the crystallinity of the starting material is the comparison of the relative intensities of the d-spacing of their respective X-ray powder diffraction patterns. The sum of the peak intensities, in arbitrary units above the background, of the starting material is used as the standard and is compared with the corresponding peak intensities of the products. When, for example, the numerical sum of the peak heights of the molecular sieve product is 85 percent of the value of the sum of the peak intensities of the starting zeolite, then 85 percent of the crystallinity has been retained. In practice it is common to utilize only a portion of the peaks for this purpose, as for example, five or six of the strongest peaks. Other indications of the retention of crystallinity are surface area and adsorption capacity. These tests may be preferred when the substituted metal significantly changes, e.g., increases, the absorption of x-rays by the sample or when peaks experience substantial shifts such as in the dealumination process.

After having undergone any of the dealumination treatments as described above, the UZM-8HS is usually dried and can be used in various processes as discussed below. Applicants have found the properties of the UZM-8HS can be further modified by one or more additional treatment. These treatments include steaming, calcining or ion exchanging and can be carried out individually or in any combination. Some of these combinations include but are not limited to:

steam ⟶ calcine ⟶ ion exchange;

calcine ⟶ steam ⟶ ion exchange;

ion exchange ⟶ calcine ⟶ steam ion exchange ⟶ steam ⟶ calcine;

steam ⟶ calcine;

calcine ⟶ steam, etc.

The dealumination treatment described above can be combined in any order to provide the zeolites of the invention although not necessarily with equivalent result. It should be pointed out that the particular sequence of treatments, e.g., AFS, acid extraction, steaming, calcining, etc can be repeated as many times as necessary to obtain the desired properties. Of course one treatment can be repeated while not repeating other treatments, e.g., repeating the AFS two or more times before carrying out steaming or calcining; etc. Finally, the sequence and/or repetition of treatments will determine the properties of the final UZM-8HS composition.

The UZM-8HS as prepared above is described by the empirical formula on an anhydrous basis of:

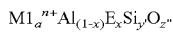

$$M1_a^{n+}Al_{(1-x)}E_xSi_{y'}O_{z''}$$

where M1 is at least one exchangeable cation selected from the group consisting of alkali, alkaline earth metals, rare earth metals, ammonium ion, hydrogen ion and mixtures thereof, a is the mole ratio of M1 to (Al+E) and varies from about 0.05 to about 50, n is the weighted average valence of M1 and has a value of about +1 to about +3, E is an element selected from the group consisting of gallium, iron, boron, chromium, indium and mixtures thereof, x is the mole fraction of E and varies from 0 to 1.0, y' is the mole ratio of Si to (Al+E) and varies from greater than about 6.5 to virtually pure silica and z'' is the mole ratio of O to (Al+E) and has a value determined by the equation:

$$z''=(a \cdot n+3+4 \cdot y')/2.$$

By virtually pure silica is meant that virtually all the aluminum and/or the E metals have been removed from the framework. It is well known that it is virtually impossible to remove all the aluminum and/or E metal. Numerically, a zeolite is virtually pure silica when y' has a value of at least 3,000, preferably 10,000 and most preferably 20,000. Thus, ranges for y' are from 6.5 to 3,000 preferably greater than 10 to about 3,000; 6.5 to 10,000 preferably greater than 10 to about 10,000 and 6.5 to 20,000 preferably greater than 10 to about 20,000.

In specifying the proportions of the zeolite starting material or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The UZM-8HS zeolite obtained after one or more of the above described treatments will have x-ray diffraction patterns which are different (and thus unique) from that of UZM-8. A list of the major peaks that are common to all the UZM-8HS materials is given in Table B.

TABLE B

| UZM-8HS | | |
|---|---|---|
| 2-θ | d(Å) | $I/I_o$% |
| 6.90-7.40 | 12.80-11.94 | w-vs |
| 8.15-8.66 | 10.84-10.21 | m-vs |
| 14.10-14.70 | 6.28-6.02 | w-vs |
| 19.40-20.10 | 4.57-4.41 | w-s |
| 22.00-22.85 | 4.04-3.89 | m-vs |
| 24.65-25.40 | 3.61-3.50 | w-m |
| 25.70-26.50 | 3.46-3.36 | w-vs |

The zeolites of this invention are capable of separating mixtures of molecular species based on the molecular size (kinetic diameter) or on the degree of polarity of the molecular species. When the separation of molecular species is based on molecular size, separation is accomplished by the smaller molecular species entering the intracrystalline void space while excluding larger species. The kinetic diameters of various molecules such as oxygen, nitrogen, carbon dioxide, carbon monoxide and various hydrocarbons are provided in D. W. Breck, Zeolite Molecular Sieves, John Wiley and Sons (1974) p. 636. The separation of hydrocarbons based on molecular size is a preferred application.

The hydrocarbon conversion processes in which the UZM-8HS can be used either as catalysts or catalyst supports are any of those well known in the art. These include without limitation cracking, hydrocracking, alkylation of both aromatics and isoparaffins, isomerization, polymerization, reforming, dewaxing, hydrogenation, dehydrogenation, transalkylation, dealkylation, hydration, dehydration, hydrotreating, hydrodenitrogenation, hydrodesulfurization, methanation and syngas shift process. Preferred hydrocarbon conversion processes are transalkylation of aromatics, alkylation of aromatics and isoparaffins and isomerization of aromatics.

For use in the hydrocarbon conversion processes described herein, the zeolite preferably is mixed with a binder for convenient formation of catalyst particles in a proportion of about 5 to 100 mass % zeolite and 0 to 95 mass-% binder, with the zeolite preferably comprising from about 10 to 90 mass-% of the composite. The binder should preferably be porous, have a surface area of about 5 to about 800 m$^2$/g, and be relatively refractory to the conditions utilized in the hydrocarbon conversion process. Non-limiting examples of binders are aluminas, titania, zirconia, zinc oxide, magnesia, boria, silica-alumina, silica-magnesia, chromia-alumina, alumina-boria, silica-zirconia, etc.; silica, silica gel, and clays. Preferred binders are amorphous silica and alumina, including gamma-, eta-, and theta-alumina, with gamma- and eta-alumina being especially preferred.

The zeolite with or without a binder can be formed into various shapes such as pills, pellets, extrudates, spheres, etc. Preferred shapes are extrudates and spheres. Extrudates are prepared by conventional means which involves mixing of zeolite either before or after adding metallic components, with the binder and a suitable peptizing agent to form a homogeneous dough or thick paste having the correct moisture content to allow for the formation of extrudates with acceptable integrity to withstand direct calcination. The dough then is extruded through a die to give the shaped extrudate. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

Spheres can be prepared by the well known oil-drop method which is described in U.S. Pat. No. 2,620,314 which is incorporated by reference. The method involves dropping a mixture of zeolite, and for example, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50-200° C. and subjected to a calcination procedure at a temperature of about 450-700° C. for a period of about 1 to about 20 hours. This treatment effects conversion of the hydrogel to the corresponding alumina matrix.

For isomerization of xylenes the catalyst will also include a platinum-group metal, including one or more of platinum, palladium, rhodium, ruthenium, osmium, and iridium, as an essential component of the present catalyst. The preferred platinum-group metal is platinum. The platinum-group metal component may exist within the final catalyst composite as a compound such as an oxide, sulfide, halide, oxysulfide, etc., or as an elemental metal or in combination with one or more other ingredients of the catalyst composite. It is believed that the best results are obtained when substantially all the platinum-group metal component exists in a reduced state. The platinum-group metal component generally comprises from about 0.01 to about 5 mass-% and preferably from about 0.1 to about 2% of the final catalyst composite, calculated on an elemental basis.

The platinum-group metal component may be incorporated into the catalyst composite in any suitable manner. One method of preparing the catalyst involves the utilization of a water-soluble, decomposable compound of a platinum-group metal to impregnate the calcined sieve/binder composite. Alternatively, a platinum-group metal compound may be added at the time of compositing the zeolite and binder. Yet another method of effecting a suitable metal distribution is by compositing the metal component with the binder prior to co-extruding the zeolite and binder. Complexes of platinum-group metals which may be employed according to the above or other known methods include chloroplatinic acid, chloropalladic acid, ammonium chloroplatinate, bromoplatinic acid, platinum trichloride, platinum tetrachloride hydrate, platinum dichlorocarbonyl dichloride, tetrammine platinic chloride, dinitrodiaminoplatinum, sodium tetranitroplatinate (II), palladium chloride, palladium nitrate, palladium sulfate, diamminepalladium (II) hydroxide, tetramminepalladium (II) chloride, and the like.

It is within the scope of the present invention that the catalyst composite may contain other metal components known to modify the effect of the platinum-group metal component. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalyst by any means known in the art to effect a homogeneous or stratified distribution.

The catalyst composite of the present invention may contain a halogen component. The halogen component may be either fluorine, chlorine, bromine or iodine or mixtures thereof, with chlorine being preferred. The halogen component is generally present in a combined state with the inorganic-oxide support. The optional halogen component is preferably well dispersed throughout the catalyst and may comprise from more than 0.2 to about 15 wt. %, calculated on an elemental basis, of the final catalyst. The halogen component may be incorporated in the catalyst composite in any suitable manner, either during the preparation of the inorganic-oxide support or before, while or after other catalytic components are incorporated.

The catalyst composite is dried at a temperature of from about 100° to about 320° C. for a period of from about 2 to about 24 or more hours and, usually, calcined at a temperature of from 400° to about 650° C. in an air atmosphere for a period of from about 1 to about 10 hours until the metallic compounds present are converted substantially to the oxide form. If desired, the optional halogen component may be adjusted by including a halogen or halogen-containing compound in the air atmosphere.

The resultant calcined composite optimally is subjected to a substantially water-free reduction step to insure a uniform and finely divided dispersion of the optional metallic components. The reduction optionally may be effected in situ. Substantially pure and dry hydrogen (i.e., less than 20 vol. ppm H$_2$O) preferably is used as the reducing agent in this step. The reducing agent contacts the catalyst at conditions, including a temperature of from about 200° to about 650° C. and for a period of from about 0.5 to about 10 hours, effective to reduce substantially all of the Group VIII metal component to the metallic state. In some cases the resulting reduced catalyst composite may also be beneficially subjected to presulfiding by a method known in the art to incorporate in the catalyst composite from about 0.05 to about 1.0 mass-% sulfur calculated on an elemental basis.

The feedstock to aromatics isomerization comprises isomerizable alkylaromatic hydrocarbons of the general formula $C_6H_{(6-n)}Rn$, where n is an integer from 1 to 5 and R is $CH_3$, $C_2H_5$, $C_3H_7$, or $C_4H_9$, in any combination and including all the isomers thereof to obtain more valuable isomers of the alkylaromatic. Suitable alkylaromatic hydrocarbons include without limitation ortho-xylene, meta-xylene, para-xylene, ethylbenzene, ethyltoluenes, tri-methylbenzenes, di-ethylbenzenes, tri-ethyl-benzenes, methylpropylbenzenes, ethylpropylbenzenes, di-isopropylbenzenes, and mixtures thereof.

Isomerization of a $C_8$-aromatic mixture containing ethylbenzene and xylenes is a particularly preferred application for the zeolites of the invention. Generally such mixture will have an ethylbenzene content in the approximate range of 5 to 50 mass-%, an ortho-xylene content in the approximate range of 0 to 35 mass-%, a meta-xylene content in the approximate range of 20 to 95 mass-% and a para-xylene content in the approximate range of 0 to 15 mass-%. It is preferred that the aforementioned $C_8$ aromatics comprise a non-equilibrium mixture, i.e., at least one $C_8$-aromatic isomer is present in a concentration that differs substantially (defined herein as a difference of at least 5 mass-% of the total $C_8$ aromatics) from the thermodynamic equilibrium concentration of that isomer at isomerization conditions. Usually the non-equilibrium mixture is prepared by removal of para- and/or ortho-xylene from a fresh $C_8$ aromatic mixture obtained from an aromatics-production process, and preferably the non-equilibrium mixture contains less than 5 mass-% para-xylene.

The alkylaromatic hydrocarbons may be utilized in the present invention as found in appropriate fractions from various refinery petroleum streams, e.g., as individual components or as certain boiling-range fractions obtained by the selective fractionation and distillation of catalytically cracked or reformed hydrocarbons. The isomerizable aromatic hydrocarbons need not be concentrated; the process of this invention allows the isomerization of alkylaromatic-containing streams such as catalytic reformate with or without subsequent aromatics extraction to produce specified xylene isomers and particularly to produce para-xylene. A $C_8$-aromatics feed to the present process may contain nonaromatic hydrocarbons, i.e., naphthenes and paraffins, in an amount up to 30 mass-%. Preferably the isomerizable hydrocarbons consist essentially of aromatics, however, to ensure pure products from downstream recovery processes.

According to the process of the present invention, an alkylaromatic hydrocarbon feed mixture, preferably in admixture with hydrogen, is contacted with a catalyst of the type hereinafter described in an alkylaromatic hydrocarbon isomerization zone. Contacting may be effected using the catalyst in a fixed-bed system, a moving-bed system, a fluidized-bed system, or in a batch-type operation. In view of the danger of attrition loss of the valuable catalyst and of the simpler operation, it is preferred to use a fixed-bed system. In this system, a hydrogen-rich gas and the feed mixture are preheated by suitable heating means to the desired reaction temperature and then passed into an isomerization zone containing a fixed bed of catalyst. The conversion zone may be one or more separate reactors with suitable means therebetween to ensure that the desired isomerization temperature is maintained at the entrance to each zone. The reactants may be contacted with the catalyst bed in either upward-, downward-, or radial-flow fashion, and the reactants may be in the liquid phase, a mixed liquid-vapor phase, or a vapor phase when contacted with the catalyst.

The alkylaromatic feed mixture, preferably a non-equilibrium mixture of $C_8$ aromatics, is contacted with the isomerization catalyst at suitable alkylaromatic-isomerization conditions. Such conditions comprise a temperature ranging from about 0° to 600° C. or more, and preferably is in the range of from about 100° to 500° C. The pressure generally is from about 1 to 100 atmospheres absolute, preferably less than about 50 atmospheres. Sufficient catalyst is contained in the isomerization zone to provide a liquid hourly space velocity with respect to the hydrocarbon feed mixture of from about 0.1 to 30 $hr^{-1}$, and preferably 0.5 to 10 $hr^{-1}$. The hydrocarbon feed mixture optimally is reacted in admixture with hydrogen at a hydrogen/hydrocarbon mole ratio of about 0.5:1 to about 25:1 or more. Other inert diluents such as nitrogen, argon and light hydrocarbons may be present.

The reaction proceeds via the mechanism, described hereinabove, of isomerizing xylenes while reacting ethylbenzene to form a xylene mixture via conversion to and reconversion from naphthenes. The yield of xylenes in the product thus is enhanced by forming xylenes from ethylbenzene. The loss of $C_8$ aromatics through the reaction thus is low: typically less than about 4 mass-% per pass of $C_8$ aromatics in the feed to the reactor, preferably about 3 mass-% or less, and most preferably no more than about 2.5 mass-%.

The particular scheme employed to recover an isomerized product from the effluent of the reactors of the isomerization zone is not deemed to be critical to the instant invention, and any effective recovery scheme known in the art may be used. Typically, the reactor effluent will be condensed and the hydrogen and light-hydrocarbon components removed therefrom by flash separation. The condensed liquid product then is fractionated to remove light and/or heavy byproducts and obtain the isomerized product. In some instances, certain product species such as ortho-xylene may be recovered from the isomerized product by selective fractionation. The product from isomerization of $C_8$ aromatics usually is processed to selectively recover the para-xylene isomer, optionally by crystallization. Selective adsorption is preferred using crystalline aluminosilicates according to U.S. Pat. No. 3,201,491. Improvements and alternatives within the preferred adsorption recovery process are described in U.S. Pat. Nos. 3,626,020, 3,696,107, 4,039,599, 4,184,943, 4,381,419 and 4,402,832, incorporated herein by reference thereto.

In a separation/isomerization process combination relating to the processing of an ethylbenzene/xylene mixture, a fresh $C_8$-aromatics feed is combined with isomerized product comprising $C_8$ aromatics and naphthenes from the isomerization reaction zone and fed to a para-xylene separation zone; the para-xylene-depleted stream comprising a non-equilibrium mixture of $C_8$ aromatics is fed to the isomerization reaction zone, where the $C_8$-aromatic isomers are isomerized to near-equilibrium levels to obtain the isomerized product. In this process scheme non-recovered $C_8$-aromatic isomers preferably are recycled to extinction until they are either converted to para-xylene or lost due to side-reactions. Ortho-xylene separation, preferably by fractionation, also may be effected on the fresh $C_8$-aromatic feed or isomerized product, or both in combination, prior to para-xylene separation.

The alkylation and preferably the monoalkylation of aromatic compounds involve reacting an aromatic compound with an olefin using the above described zeolitic catalyst. The olefins which can be used in the instant process are any of those which contain from 2 up to about 30 carbon atoms. These olefins may be branched or linear olefins and either terminal or internal olefins. Preferred olefins are ethylene, propylene and those olefins which are known as detergent range olefins. Detergent range olefins are linear olefins containing from 6 up through about 20 carbon atoms which have either internal or terminal double bonds. Linear olefins containing from 8 to 16 carbon atoms are preferred and those containing from 10 up to about 14 carbon atoms are especially preferred.

The alkylatable aromatic compounds may be selected from the group consisting of benzene, naphthalene, anthracene, phenanthrene, and substituted derivatives thereof, with benzene and its derivatives being the most preferred aromatic compound. By alkylatable is meant that the aromatic compound can be alkylated by an olefinic compound. The alkylatable aromatic compounds may have one or more of the substituents selected from the group consisting of alkyl groups (having from 1 to about 20 carbon atoms), hydroxyl groups, and alkoxy groups whose alkyl group also contains from 1 up to 20 carbon atoms. Where the substituent is an alkyl or alkoxy group, a phenyl group can also be substituted on the alkyl chain. Although unsubstituted and monosubstituted benzenes, naphthalenes, anthracenes, and phenanthrenes are most often used in the practice of this invention, polysubstituted aromatics also may be employed. Examples of suitable alkylatable aromatic compounds in addition to those cited above include biphenyl, toluene, xylene, ethylbenzene, propylbenzene, butylbenzene, pentylbenzene, hexylbenzene, heptylbenzene, octylbenzene, etc.; phenol, cresol, anisole, ethoxy-, propoxy-, butoxy-, pentoxy-, hexoxybenzene, etc.

The particular conditions under which the monoalkylation reaction is conducted depends upon the aromatic compound and the olefin used. One necessary condition is that the reaction be conducted under at least partial liquid phase conditions. Therefore, the reaction pressure is adjusted to maintain the olefin at least partially dissolved in the liquid phase. For higher olefins the reaction may be conducted at autogenous pressure. As a practical matter the pressure normally is in the range between about 200 and about 1,000 psig (1379-6985 kPa) but usually is in a range between about 300-600 psig (2069-4137 kPa). The alkylation of the alkylatable aromatic compounds with the olefins in the C2-C20 range can be carried out at a temperature of about 60° C. to about 400° C., and preferably from about 90° C. to about 250° C., for a time sufficient to form the desired product. In a continuous process this time can vary considerably, but is usually from about 0.1 to about 3 hr$^{-1}$ weight hourly space velocity with respect to the olefin. In particular, the alkylation of benzene with ethylene can be carried out at temperatures of about 200° C. to about 250° C. and the alkylation of benzene by propylene at a temperature of about 90° C. to about 200° C. The ratio of alkylatable aromatic compound to olefin used in the instant process will depend upon the degree of selective monoalkylation desired as well as the relative costs of the aromatic and olefinic components of the reaction mixture. For alkylation of benzene by propylene, benzene-to-olefin ratios may be as low as about 1 and as high as about 10, with a ratio of 2.5-8 being preferred. Where benzene is alkylated with ethylene a benzene-to-olefin ratio between about 1:1 and 8:1 is preferred. For detergent range olefins of C6-C20, a benzene-to-olefin ratio of between 5:1 up to as high as 30:1 is generally sufficient to ensure the desired monoalkylation selectivity, with a range between about 8:1 and about 20:1 even more preferred.

The zeolites of this invention can also be used to catalyze transalkylation. By "transalkylation" is meant that process where an alkyl group on one aromatic nucleus is intermolecularly transferred to a second aromatic nucleus. A preferred transalkylation process is one where one or more alkyl groups of a polyalkylated aromatic compound is transferred to a nonalkylated or monoalkylated aromatic compound, and is exemplified by reaction of diisopropylbenzene with benzene to give two molecules of cumene. Thus, transalkylation often is utilized to add to the selectivity of a desired selective monoalkylation by reacting the polyalkylates invariably formed during alkylation with nonalkylated or monoalkylated aromatic to form additional monoalkylated or dialkylated products. For the purposes of this process, the polyalkylated aromatic compounds are those formed in the alkylation of alkylatable aromatic compounds with olefins as described above and include without limitation polyethylbenzene, ethylmethylbenzene, polyethyltoluene, xylene and trimethylbenzene, the nonalkylated aromatic compounds are benzene, naphthalene, anthracene, and phenanthrene and the monoalkylated aromatic compounds include toluene, methylnaphthalene, methylanthracene and methylphenanthrene. The reaction conditions for transalkylation are similar to those for alkylation, with temperatures being in the range of about 100 to about 500°, pressures in the range of 100 to about 750 psig, and the molar ratio of unalkylated aromatic to polyalkylated aromatic in the range from about 1 to about 10. Examples of polyalkylated aromatics which may be reacted with, e.g., benzene as the nonalkylated aromatic include diethylbenzene, diisopropylbenzene, dibutylbenzene, triethylbenzene, triisopropylbenzene etc.

Hydrocracking conditions typically include a temperature in the range of 400° to 1200° F. (204-649° C.), preferably between 600° and 950° F. (316-510° C.). Reaction pressures are in the range of atmospheric to about 3,500 psig (24,132 kPa g), preferably between 200 and 3000 psig (1379-20,685 kPa g). Contact times usually correspond to liquid hourly space velocities (LHSV) in the range of about 0.1 hr$^{-1}$ to 15 hr$^{-1}$, preferably between about 0.2 and 3 hr$^{-1}$. Hydrogen circulation rates are in the range of 1,000 to 50,000 standard cubic feet (scf) per barrel of charge (178-8,888 std. m$^3$/m$^3$), preferably between 2,000 and 30,000 scf per barrel of charge (355-5,333 std. m$^3$/m$^3$). Suitable hydrotreating conditions are generally within the broad ranges of hydrocracking conditions set out above.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the UZM-8 composition using feedstocks such as gas oils, heavy naphthas, deasphalted crude oil residua, etc. with gasoline being the principal desired product. Temperature conditions of 850° to 1100° F., LHSV values of 0.5 to 10 and pressure conditions of from about 0 to 50 psig are suitable.

Alkylation of isoparaffins with olefins to produce alkylates suitable as motor fuel components is carried out at temperatures of −30° to 40° C., pressures from about atmospheric to about 6,894 kPa (1,000 psig) and a weight hourly space velocity (WHSV) of 0.1 to about 120. Details on paraffin alkylation may be found in U.S. Pat. Nos. 5,157,196 and 5,157,197, which are incorporated by reference.

The structures of the UZM-8 and UZM-8HS zeolites of this invention were determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were either continuously scanned at 2° to 70° (2θ) or in a step mode from 4° to 35° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of $100\% \times I/I_o$, the above designations are defined as:

w=0-15; m=15-60: s=60-80 and vs=80-100

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

EXAMPLES

The following abbreviations will be used in the examples:
Al (Oi-Pr)$_3$—aluminum isopropoxide
Al (Osec-Bu)$_3$—aluminum tri-sec-butoxide
DEDMAOH—diethyldimethylammonium hydroxide
ETMAOH—ethyltrimethylammonium hydroxide
HM(OH)$_2$—hexamethonium dihydroxide
MTEAOH—methyltriethylammonium hydroxide
TEAOH—tetraethylammonium hydroxide
TEOS—tetraethylorthosilicate
TMACl—tetramethylammonium chloride
TPAOH—tetrapropylammonium hydroxide Example 1

An aluminosilicate reaction mixture was prepared in the following manner. Al(Osec-Bu)$_3$ (97%), 66.51 g, was added to 918.29 g of DEDMAOH, (20% aq) with vigorous stirring. To this mixture, 208.95 g precipitated silica, (Ultrasil™ VN SP3, 89% SiO$_2$) was added with continuous mixing. A solution of 37.2 g Na$_2$SO$_4$ in 169.05 g deionized H$_2$O was prepared and added to the previous mixture and homogenized for 10 min. A 1.7 g portion of UZM-8 seed was added to the mixture, followed by an additional 20 min of mixing. A 1077.3 g portion of this final reaction mixture was transferred to a 2-L Teflon-lined autoclave. The autoclave was placed in an oven set at 150° C. and the reaction mixture was digested quiescently for 10 days. The solid product was collected by filtration, washed with de-ionized water, and dried at 95° C.

The product was identified as UZM-8 by powder x-ray diffraction analysis. Table 1 below shows the characteristic diffraction lines for the product. Elemental analysis revealed the composition of the isolated product to consist of the elemental mole ratios Si/Al=9.96, Na/Al=0.26, N/Al=1.23, and C/N=4.83. A portion of the material was calcined by ramping to 538° C. in N$_2$ for 3 hr followed by a 4 hr dwell in N$_2$. The stream was then switched to air and the sample was calcined for another 15 hr at 538° C. The calcined sample was then ammonium ion-exchanged to remove the alkali cations. The sample was then reactivated by heating to 500° C. in air and holding at that temperature for 2 hr. The BET surface area was found to be 343 m$^2$/g and the micropore volume was 0.14 cc/g.

TABLE 1

| 2-θ | d(Å) | I/I$_0$ % |
|---|---|---|
| 3.00 | 29.39 | s |
| 6.71 | 13.17 | m |
| 7.16 | 12.34 | m |
| 8.52 | 10.37 | vs |
| 13.06 | 6.77 | w |
| 14.39 | 6.15 | w |
| 15.80 | 5.60 | w |
| 20.01 | 4.43 | m |
| 22.18 | 4.00 | vs |
| 25.03 | 3.55 | m |
| 25.98 | 3.43 | vs |
| 26.95 | 3.31 | m |
| 28.87 | 3.09 | w-m |
| 31.43 | 2.84 | w |
| 33.35 | 2.68 | w |
| 37.65 | 2.39 | w |
| 44.50 | 2.03 | w |
| 46.15 | 1.97 | w |
| 46.36 | 1.96 | w |
| 48.43 | 1.88 | w |
| 51.64 | 1.77 | w |
| 61.04 | 1.52 | w |
| 65.34 | 1.43 | w |

Example 2

An aluminosilicate reaction mixture was prepared by adding 80.44 g of Al(Osec-Bu)$_3$ (95+%) to 732.97 g of DEDMAOH (20%) with vigorous stirring. This was followed by the addition of 252.7 g of Ultrasil VN SP (85%) silica. Then a solution containing 12.67 g NaOH dissolved in 321.22 g distilled water was prepared and added slowly to the aluminosilicate reaction mixture with continued vigorous stirring. The mixture was homogenized for 30 minutes with a high-speed stirrer. After a half-hour of homogenizing the reaction mixture, 16 g of UZM-8 seeds were added. The reaction mixture was placed in a 2 L stirred autoclave at 150° C. for 185 hours. The solid product was isolated by filtration, washed with de-ionized water, and dried at room temperature.

X-ray powder diffraction analysis showed the product to have the UZM-8 structure. Characteristic diffraction lines for the product are shown in Table 2 below. The UZM-8 sample was ammonium ion-exchanged with a solution that contained 1 g NH$_4$NO$_3$ dissolved in 10 g de-ionized water for every gram of UZM-8. The exchanges were carried out twice, heating for 2 hr at 80° C. each time, with thorough washes in between. A portion of the exchanged product was calcined under a flow of nitrogen for 6 hr at 540° C. The composition of the calcined product exhibited the elemental mole ratio Si/Al=9.47 as determined by elemental analysis. The BET surface area of the calcined material was 427 m$^2$/g and the micropore volume was 0.11 cc/g.

TABLE 2

| 2-θ | d(Å) | I/I$_o$ % |
|---|---|---|
| 2.88 | 30.61 | m |
| 6.56 | 13.46 | m |
| 7.12 | 12.40 | s |
| 8.52 | 10.37 | vs |
| 12.78 | 6.92 | w |
| 13.36 | 6.62 | w |
| 14.39 | 6.15 | w |
| 19.80 | 4.48 | m |
| 22.16 | 4.01 | s |
| 24.90 | 3.57 | m |
| 25.90 | 3.44 | vs |
| 26.36 | 3.38 | m |
| 33.25 | 2.69 | w |
| 37.64 | 2.39 | w |
| 45.87 | 1.98 | w |
| 48.60 | 1.87 | w |
| 51.53 | 1.77 | w |
| 65.24 | 1.43 | w |

Example 3

A 23 g portion of the UZM-8 ammonium exchanged composition from example 2 was acid treated as follows. An acidic solution was prepared by diluting 50 g HNO$_3$ (69%) in 88 g de-ionized water. The solution was heated to 98° C. before the addition of the ammonium exchanged UZM-8. The resulting slurry was stirred for 4 hr at 98° C. The product was isolated by filtration, washed with de-ionized water, and dried at 98° C.

The modified product was determined to be UZM-8HS via x-ray powder diffraction analysis. Characteristic diffraction lines for the product are listed in Table 3. Elemental analyses showed the product to have a Si/Al ratio of 22.2. The sample was calcined at 540° C. under nitrogen for 6 hrs. The BET surface area of acid extracted UZM-8 was 515 m$^2$/g with a micropore volume of 0.14 cc/g.

TABLE 3

| 2-θ | d(Å) | I/I$_o$ % |
|---|---|---|
| 4.71 | 18.76 | w |
| 7.21 | 12.25 | s |
| 8.58 | 10.30 | vs |
| 14.50 | 6.10 | m |
| 19.88 | 4.46 | m |
| 22.50 | 3.95 | vs |
| 25.15 | 3.54 | m |
| 26.10 | 3.41 | s |
| 26.82 | 3.32 | m |
| 33.54 | 2.67 | w |
| 46.32 | 1.96 | w |
| 48.94 | 1.86 | w |
| 52.12 | 1.75 | w |
| 65.73 | 1.42 | w |

Example 4

A UZM-8 sample was prepared according to Example 1 above, providing a product with a Si/Al ratio of 9.4 and was ammonium ion-exchanged (1225 ml of 1.25M NH$_4$NO$_3$ heated to 75° C. for 2 h and repeated). The sample was then formulated into a catalyst comprising 70 wt % UZM-8 and 30 wt % alumina. The extrusion was done using HNO$_3$-peptized Al$_2$O$_3$ as a binder and Solka Floc™ as an extrusion aid to obtain 1/16" diameter extrudates. The extrudates were activated in a muffle oven by heating to 538° C. and holding there for one hour in a N$_2$ flow, and then switching to air and holding for 15 hours.

Example 5

UZM-8HS was prepared as per Example 3. It was formulated into a catalyst consisting of 70 wt % zeolite and 30 wt % Al$_2$O$_3$. The extrusion was done using HNO$_3$-peptized Al$_2$O$_3$ as a binder and Solka Floc™ as an extrusion aid to obtain 1/16" diameter extrudates. The extrudates were activated in a muffle oven by first heating to 538° C. and holding there for one hour in a N$_2$ flow, and then switching to air and holding for 15 hours.

Example 6

The catalysts of Examples 4 and 5 were tested for ethylbenzene (EB) synthesis via the alkylation of benzene with ethylene. The catalysts were tested in the once through mode without product effluent recycle. Variables in the tests included inlet temperature and benzene to ethylene ratio. The performance of the UZM-8 and -8HS catalysts is summarized in Table 4. The data clearly show that the UZM-8 and -8HS derived catalysts give good mono-alkylated and total alkylated product selectivity. After testing the UZM-8HS catalyst was regenerated at 540° C. in an air flow to remove the carbonaceous material deposited thereon. As shown in Table 4, the performance of the regenerated catalyst was found to be comparable to the fresh catalyst.

TABLE 4

Ethylbenzene Synthesis with UZM-8/Al$_2$O$_3$ Catalyst
Conditions: 550 psig; 0.45 hr$^{-1}$ LSHV; Once through mode

| Example | Benzene/ Ethylene | Inlet Temp. (° C.) | EB Selectivity | EB + DEB + TEB + TeEB* (Total Alkylate) |
|---|---|---|---|---|
| 4 | 9.6 | 220 | 92.9 | 99.9 |
| 4 | 9.4 | 200 | 93.5 | 99.9 |
| 4 | 6.6 | 180 | 91.2 | 99.9 |
| 5 | 8.9 | 220 | 93.5 | 99.9 |
| 5 | 8.9 | 200 | 94.1 | 99.9 |
| 5 | 6.3 | 180 | 92.7 | 99.9 |
| 5 regenerated | 8.7 | 220 | 92.8 | 99.8 |
| 5 regenerated | 8.4 | 200 | 93.6 | 99.9 |
| 5 regenerated | 6.1 | 180 | 91.7 | 99.9 |

*DEB = Diethylbenzene; TEB = Triethylbenzene; TeEB = Tetraethylbenzene

Example 7

An aluminosilicate reaction mixture was prepared by adding 80.44 g of Al (Osec-Bu)$_3$ (95+%) to 732.97 g of DEDMAOH (20%) with vigorous stirring. This was followed by the addition of 252.7 g of Ultrasil™ VN SP (85%) silica. A solution containing 12.67 g NaOH dissolved in 321.22 g distilled water was prepared and added slowly to the aluminosilicate mixture with mixing. The resultant mixture was homogenized for 30 minutes with a high-speed stirrer. The reaction mixture was placed in a 2 L stirred autoclave at 150° C. for 285 hours at autogenous pressure. The solid product was isolated by filtration, washed with distilled water, and dried at room temperature.

Analysis by powder x-ray diffraction showed the product to have the UZM-8 structure. Characteristic diffraction lines for the product are listed in Table 5. The UZM-8 sample was ammonium ion-exchanged using a solution that contained 1 g NH$_4$NO$_3$ dissolved in 10 g de-ionized water for every gram of UZM-8. The exchange was carried out twice at 80° C. for two hr, with thorough washing following each exchange. A portion of the product was calcined under a flow of nitrogen for 6 hr at 540° C. The composition of the calcined product exhibited the following mole ratios as determined by elemental analysis: Si/Al=10.51, and Na/Al=0.015. The BET surface area of the calcined material was 432 m$^2$/g and the micropore volume was 0.14 cc/g.

TABLE 5

| 2-θ | d(Å) | I/I$_o$% |
| --- | --- | --- |
| 3.02 | 29.23 | m |
| 6.52 | 13.54 | m |
| 7.08 | 12.47 | s |
| 8.56 | 10.32 | vs |
| 13.11 | 6.75 | w |
| 14.31 | 6.19 | w |
| 19.94 | 4.45 | s |
| 22.34 | 3.98 | vs |
| 24.94 | 3.57 | m |
| 25.92 | 3.43 | vs |
| 26.44 | 3.37 | m |
| 31.44 | 2.84 | w |
| 33.32 | 2.69 | w |
| 36.28 | 2.47 | w |
| 37.64 | 2.39 | w |
| 45.99 | 1.97 | w |
| 48.16 | 1.89 | w |
| 52.06 | 1.76 | w |
| 65.27 | 1.43 | w |

Examples 8-27

The following examples present various preparations of UZM-8HS. Table 6 presents a summary of all the experiments showing the parent materials, treatment sequence and Si/Al ratio. Details for each example are presented below.

TABLE 6

Modified UZM-8 Materials: Parent UZM-8, Modification Scheme, Si/Al ratio

| Example | Parent Material | Modification Steps in order | Si/Al |
| --- | --- | --- | --- |
| 8 | Example 7 w/seed | NH$_4^+$ - Cal - AW - Cal | 24.3 |
| 9 | Example 2 | NH$_4^+$ - AW - Cal | 29.28 |
| 10 | Example 7, w/seed | NH$_4^+$ - AW - Cal | 22.44 |
| 11 | Example 7, w/seed | NH$_4^+$ - Cal | 10.35 |
| 12 | Example 2 | NH$_4^+$ - Cal | 10.11 |
| 13 | Example 7, w/seed | NH$_4^+$ - AFS - Cal | 11.89 |
| 15 | Example 2 | NH$_4^+$ - Cal | 10.11 |
| 16 | Example 2 | NH$_4^+$ - AW - Cal | 19.74 |
| 17 | Example 7 | AW - Cal | ND |
| 19 | Example 2 | NH$_4^+$ - Cal | 9.82 |
| 20 | Example 2 | NH$_4^+$ - Cal - AW - Cal | 13.15 |
| 21 | Example 7 | NH$_4^+$ - Cal - AW - Cal | 18.46 |
| 22 | Example 7 | NH$_4^+$ - Cal | 11.06 |
| 23 | Example 7 | NH$_4^+$ - AFS - Cal | 17.53 |
| 25 | Example 7 | NH$_4^+$ - AFS - Cal | 18.54 |

Key:
NH$_4^+$ = Ammonium ion exchange;
Cal = calcination;
AW = acid wash;
AFS = ammonium hexafluorosilicate treatment;
ND = not determined Example 8

An ammonium exchanged UZM-8, prepared per Example 2, was calcined at 540° C. for 16 hr in air. A 12 g portion of the resulting product was suspended in a nitric acid solution (50 g HNO$_3$ (69%) diluted in 88 g deionized water) that had previously been heated to 98° C. The UZM-8 was slurried in this solution for 4 hr at 98° C., isolated by filtration, washed with deionized water and dried at 70° C. The material was then calcined at 540° C., initially in nitrogen and finally under a flow of dry air for a total of 6 hr.

Example 9

A UZM-8 sample from Example 2 was ammonium exchanged according to the procedure in Example 3. A 14 g portion of the exchanged zeolite was suspended in a nitric acid solution (35 g HNO$_3$ (69%) diluted in 120 g deionized water) that had previously been heated to 98° C. and the resulting slurry was heated for 4 hr. The product was isolated by filtration, washed with deionized water, and dried at 98° C. The product was then calcined at 540° C., initially in nitrogen and finally under a flow of dry air for a total of 6 hr.

Example 10

This material is identical to that in Example 3.

Example 11

A zeolite sample from Example 7 was ammonium exchanged using a preferred ion exchange procedure that has been applied to many of the modified materials in this application. An ammonium nitrate solution was prepared that contained 1 g NH$_4$NO$_3$ dissolved in 10 g deionized water, for each gram of zeolite to be exchanged. A slurry of the zeolite and the ammonium nitrate solution was then heated to 70° C. and held there for 2 hours. The solid was isolated and the exchange was repeated again. After the second exchange, the solid was washed with deionized water and dried. The modified zeolite was then calcined at 540° C. for 16 hr under a flow of dry air.

Example 12

A zeolite sample from Example 2 was ammonium exchanged according to the procedure in Example 11. A portion of the zeolite product was heated at 540° C. for 16 hr under a flow of dry air.

Example 13

A zeolite sample from Example 7 was ammonium exchanged according to the procedure given in Example 11. The material was then treated with ammonium hexafluorosilicate (AFS). A 3.16 g portion of (NH$_4$)$_2$SiF$_6$ was dissolved in 60.10 g deionized water. Separately, 131.45 g of the ammonium exchanged UZM-8 zeolite was slurried in 330 g deionized water and heated to 80° C. The AFS solution was then pumped into the zeolite slurry at a rate of 0.52 cc/min while maintaining the temperature at 80° C. When the addition concluded, the slurry was held at 80° C. for an additional hour. The solid was isolated by filtration, washed with 5 l deionized water and dried at room temperature. The product was calcined at 540° C. for 16 hr under a flow of dry air.

Example 14

The zeolites described in Examples 8 through 13 in the form of 20-50 mesh particles were tested for xylene isomerization per the procedure described below. For comparison purposes, a catalyst made with mordenite and $Al_2O_3$ in the shape of 1/16" diameter spheres was prepared using oil dropping technique, impregnated with Pt, calcined, reduced with $H_2$ and then sulfided at room temperature by means known in the art prior to evaluation. All the other samples were similarly reduced and sulfided. The feed composition and test conditions are set forth in Table 7. The activity is defined as the ratio of para-xylene to total xylene (PX/X) ratio, a measurement indicative of degrees to reaction advancing toward equilibrium composition. It is desirable to achieve catalytic performance of high activity (higher PX/X) and lower $C_8$ ring loss. The WHSV was adjusted to vary activity.

TABLE 7

| Process Conditions/Feed for Example 36 | |
|---|---|
| pressure, psig | 100 |
| $H_2$/feed | 4 |
| temperature, (° C.) | 365-385 |
| WHSV, $hr^{-1}$ | 3.5 |
| Feed, wt % | |
| Non-aromatics | 11.11 |
| Benzene | 0.02 |
| Toluene | 0.80 |
| Ethylbenzene | 16.25 |
| p-Xylene | 0.23 |
| m-Xylene | 48.51 |
| o-Xylene | 23.02 |
| $C_{9+}$ | 0.07 |

As shown in FIG. 1, the efficiency of xylene isomerization was greatly improved by modifications as well as by the choice of the parent UZM-8.

Example 15

The ammonium exchanged zeolite of Example 12 was mixed with alumina (20 wt % zeolite and 80 wt % alumina), extruded, calcined, loaded with 0.3 wt. % Pt calcined in air, reduced in $H_2$ and sulfided via the procedure in Example 14.

Example 16

A 300 g portion of the ammonium exchanged zeolite from example 12 was slurried in a nitric acid solution (1116 g $HNO_3$ (69%) dissolved in 700 g deionized water) that had been previously heated to 98° C. The slurry was kept at 98° C. for 3 hr, isolated by filtration and washed with deionized water. A portion of this material was mixed with alumina (20 wt % zeolite and 80 wt. % alumina), extruded, calcined, loaded with 0.3 wt % Pt calcined in air, reduced in $H_2$ and sulfided according to the procedure in Example 14.

Example 17

A 36 g portion of the zeolite from Example 7 was suspended in a nitric acid solution (100 g $HNO_3$ (69%) dissolved in 200 g deionized water) previously heated to 98° C. The slurry was held at 98° C. for 4 hr. The product was isolated by filtration, washed with deionized water, and dried at room temperature. A portion of this material was formed into an extrudate catalyst comprising 20 wt % of the zeolite and 80% alumina which was calcined, loaded with 0.3 wt % Pt calcined in air, reduced in $H_2$ and sulfided according to the procedure given in Example 14.

Example 18

Figure 2:
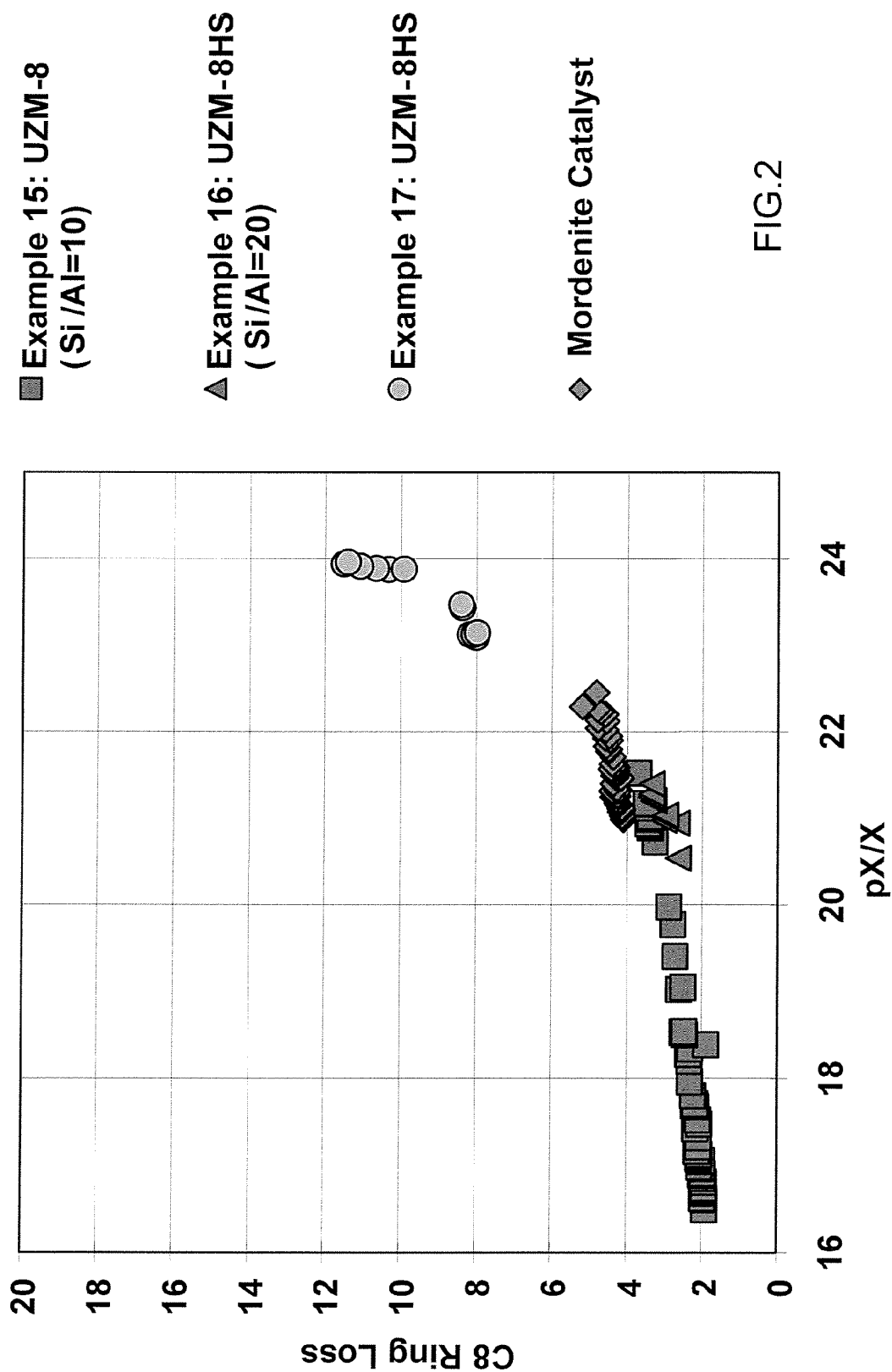
FIG. 2 presents plots of PX/X versus $C_8$ ring loss for catalysts from examples 15 to 17 and mordenite.
Figure 3:
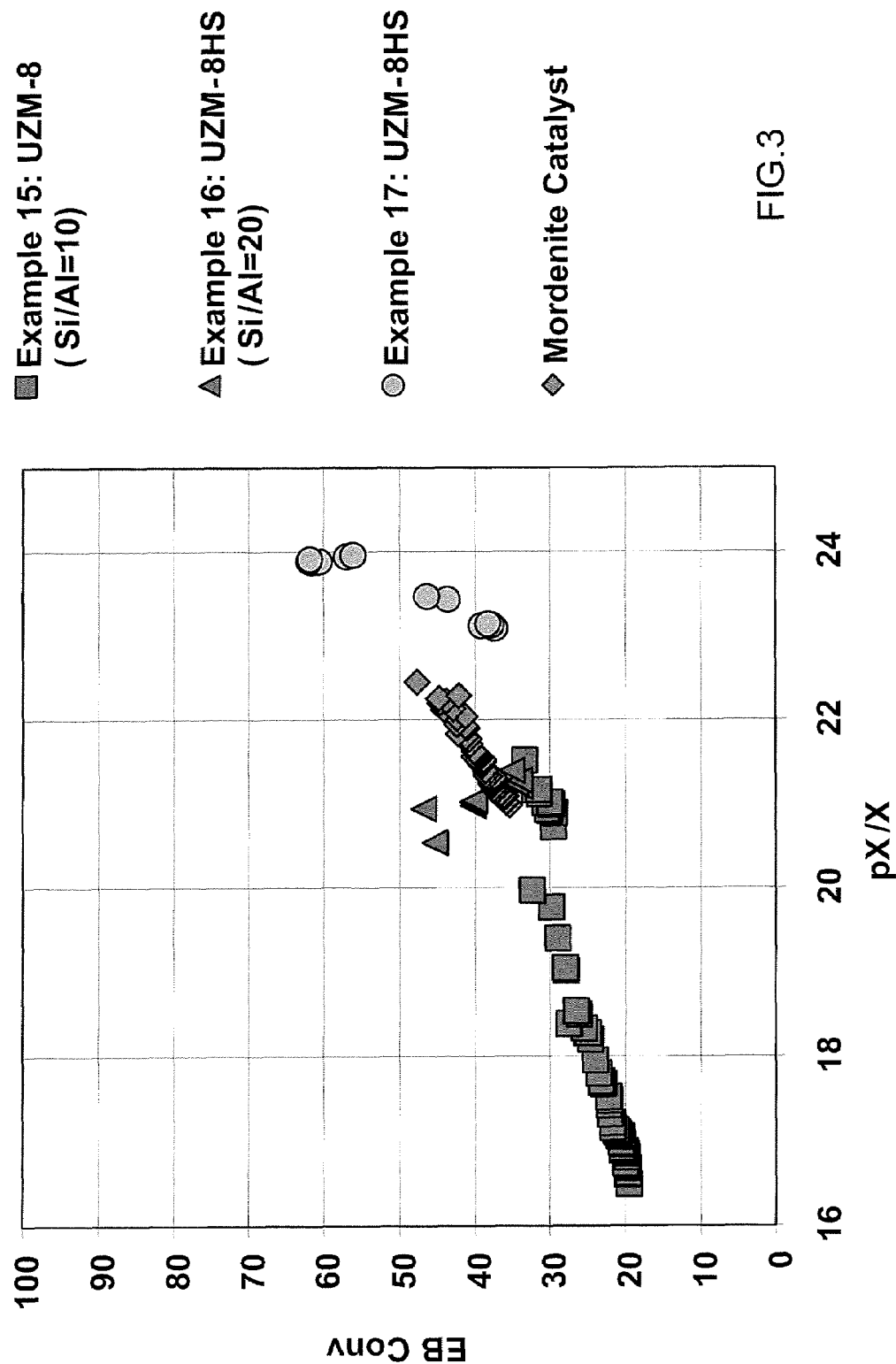
FIG. 3 presents plots of PX/X versus EB conversion for catalysts from examples 15 to 17 and mordenite.

The catalysts described in Examples 15 through 17 were evaluated for xylene and ethylbenzene isomerization performance using the test procedure of Example 14. A reference catalyst containing mordenite as per the procedure described in Example 14 was also evaluated. As shown in FIGS. 2 and 3, the performance of the UZM-8HS finished catalysts showed a dependence on the choice of parent UZM-8.

Example 19

A 75 g portion of the zeolite from Example 2 was ammonium exchanged twice using an ammonium nitrate solution (75 g $NH_4NO_3$ dissolved in 750 g deionized water) at 80° C. for 2 hr. The product was washed with deionized water and dried in air. The material was then calcined at 540° C. in flowing dry air for 10 hr.

Example 20

A 4.5 g portion of the calcined zeolite from Example 19 was additionally treated with an oxalic acid solution (6.84 g oxalic acid dissolved in 26.65 g deionized water). The oxalic acid solution was heated to 50° C. to achieve full dissolution before the zeolite was added. After the zeolite addition, the temperature of the mixture was increased to 71° C. and held there for 2 hr. The product was isolated by filtration and washed with deionized water. A portion of the dried product was calcined at 375° C. for 3 hr under flowing dry air.

Example 21

A 4.5 g portion of the calcined zeolite from Example 22 was additionally treated with an oxalic acid solution (6.84 g oxalic acid dissolved in 26.65 g deionized water). The oxalic acid solution was heated to 50° C. to achieve full dissolution before the zeolite was added. After the zeolite addition, the temperature of the mixture was increased to 71° C. and held there for 2 hr. The product was isolated by filtration and washed with deionized water. The dried product was calcined at 375° C. for 3 hr under flowing dry air.

Example 22

A 75 g portion of the zeolite from Example 7 was ammonium exchanged twice in an ammonium nitrate solution (75 g $NH_4NO_3$ dissolved in 750 g deionized water) at 80° C. for 2 hrs. The product was washed with deionized water and dried in air. A portion of the material was then calcined at 540° C. in flowing dry air for 10 hr.

Example 23

A 37 g portion of the ammonium exchanged zeolite from Example 22 (prior to calcination) was treated with ammonium hexafluorosilicate (AFS). An AFS solution was prepared by dissolving 4.35 g $(NH_4)_2SiF_6$ in 450 g deionized water. The zeolite was slurried in this solution for 17 hr at 90° C. The product was isolated by filtration, washed with deionized water and dried at 50° C.

Example 24

Figure 4:
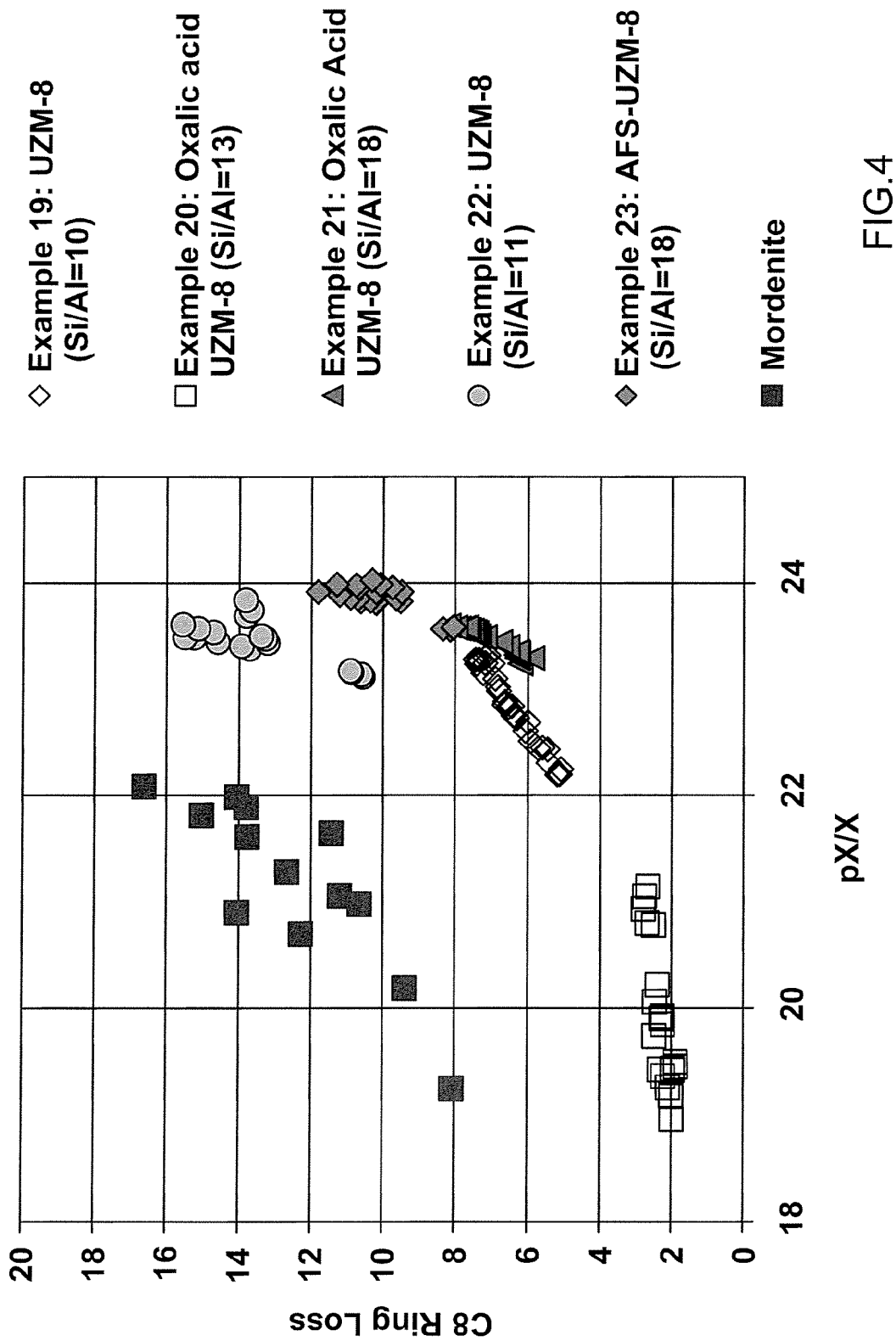
FIG. 4 presents plots of PX/X versus $C_8$ ring loss for catalysts from examples 19 to 23 and mordenite.

The zeolites from Examples 19 through 23 were formed into 20-50 mesh particulates and tested for xylene isomerization via the procedure of Example 14. As shown in FIG. 4, the efficiency of xylene isomerization was greatly improved by the modification of UZM-8 to UZM-8HS and by selection of the parent UZM-8 material.

Example 25

A 120 g portion of ammonium exchanged UZM-8 zeolite from example 7 was treated with ammonium hexafluorosilicate solution (13.9 g $(NH_4)_2SiF_6$ dissolved in 1440 g deionized water) at 90° C. for 17 hr. The product was isolated by filtration, washed with deionized water and dried. The product was calcined at 540° C. for 16 hr under a flow of dry air. The resulting AFS-UZM-8 (UZM-8HS) was mixed with alumina (10 wt % zeolite and 90 wt % $Al_2O_3$), extrudated, calcined, loaded with 0.3 wt % Pt calcined in air, reduced in $H_2$ and then sulfided.

Example 26

Figure 5:
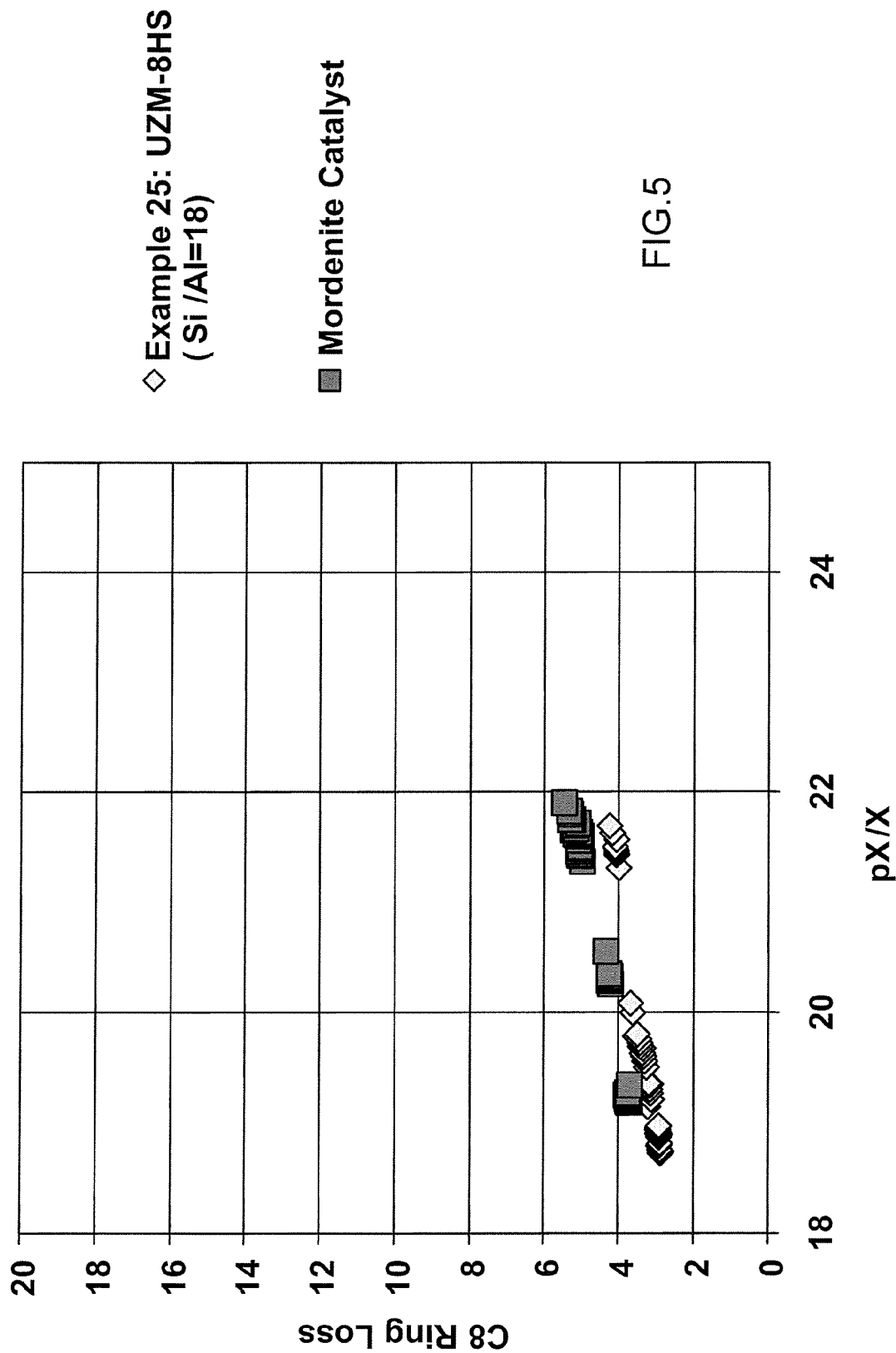
FIG. 5 presents plots of PX/X versus $C_8$ ring loss for the example 25 catalyst and mordenite.
Figure 6:
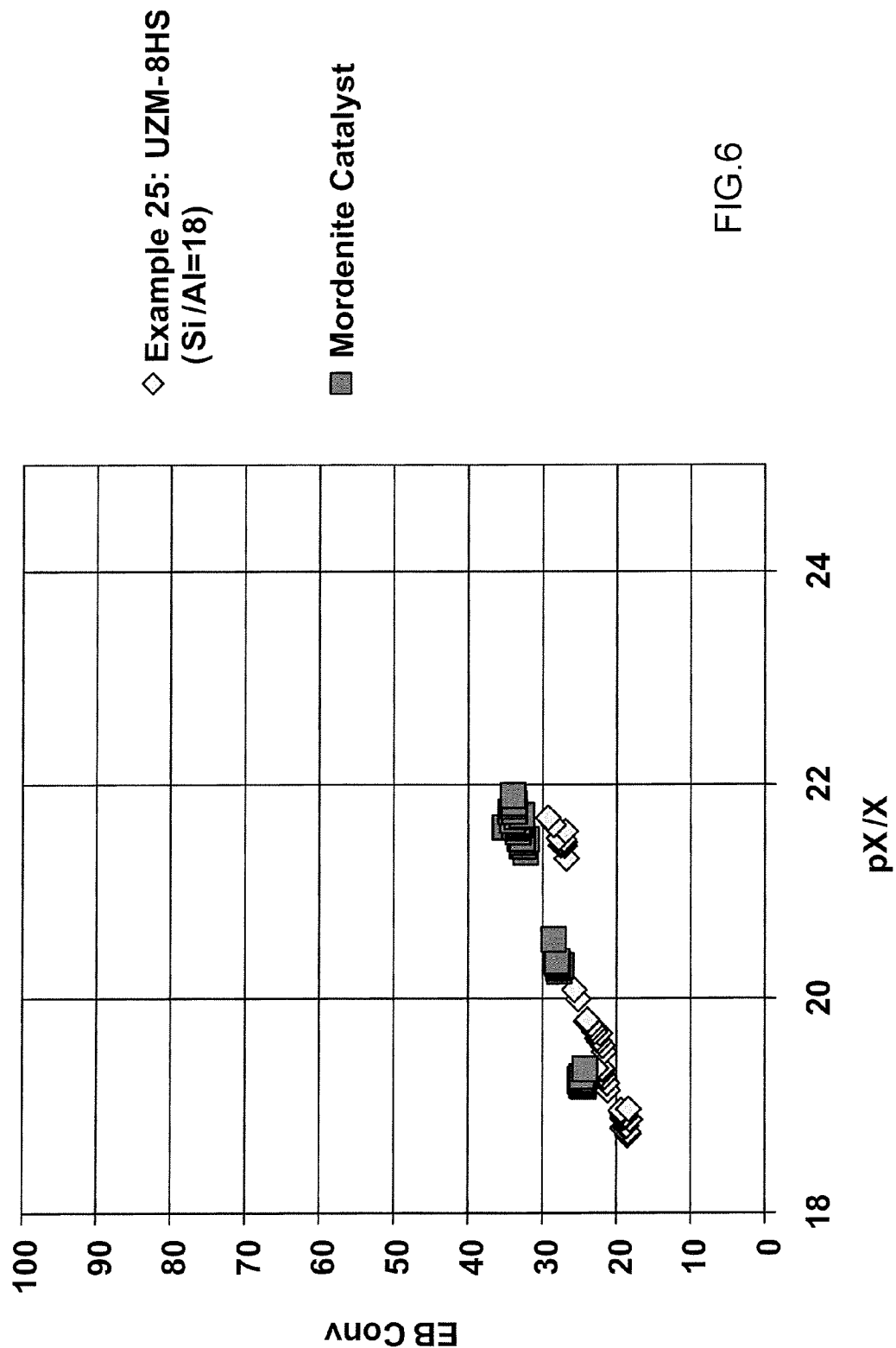
FIG. 6 presents plots of PX/X versus EB conversion for the example 25 catalyst and mordenite.

The catalyst described in Example 25 was evaluated for xylene and ethylbenzene isomerization performance as previously described. A catalyst made of mordenite was also evaluated for comparison as per Example 14. As shown in FIGS. 5 and 6, the performance of UZM-8 finished catalyst was improved by modification of UZM-8 to UZM-8HS (compare example 19 in FIG. 4).

Example 27

Figure 7:
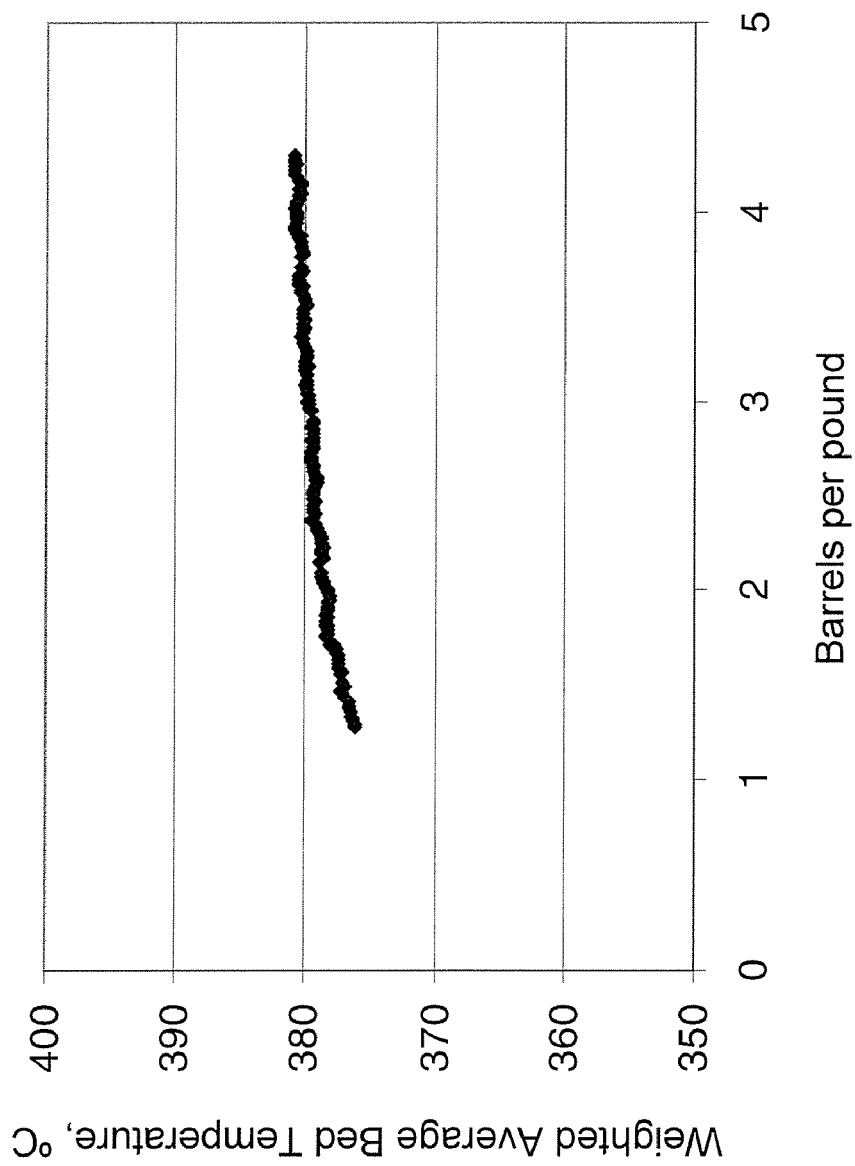
FIG. 7 presents a plot of barrels per pound (catalyst life) versus weighted average bed temperature (° C.) for the catalyst of example 25.
Figure 8:
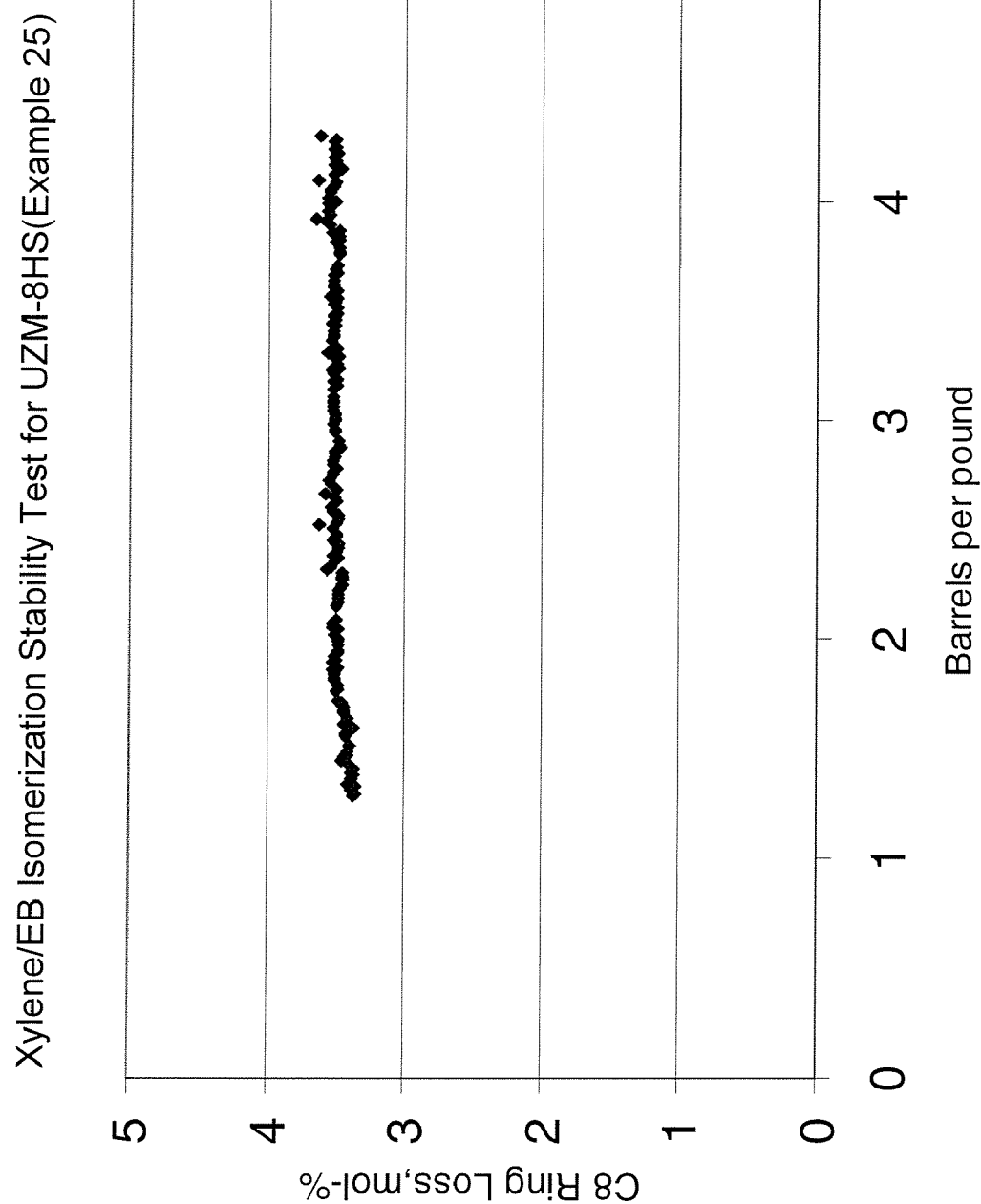
FIG. 8 presents a plot of barrels per pound versus $C_8$ ring loss for the catalyst of example 25.

The catalyst described in Example 25 was evaluated for xylene and ethylbenzene isomerization performance in an accelerated stability test to gauge the long-term stability. The feed was p-xylene depleted and contained 15 wt %EB, 52% m-xylene, 25% o-xylene with balance $C_8$ non-aromatics. The test was conducted at 4 LHSV, 4 $H_2$/HC at a constant approach to xylene isomerization equilibrium (pX/X=22.3 and oX/X=24.4). As shown in FIGS. 7 and 8, the catalyst has good stability for xylene isomerization and its $C_8$ ring loss remained constant over the duration of the test.

What is claimed is:

1. A process for the alkylation of aromatics comprising contacting a hydrocarbon stream containing an aromatic compound and an olefin with a catalytic composite at aromatic alkylation conditions to give an alkylated aromatic product, wherein the catalytic composite comprises a UZM-8HS zeolite wherein UZM-8HS has a three-dimensional framework of at least $AlO_2$ and $SiO_2$ tetrahedral units and an empirical composition on an anhydrous basis in terms of mole ratios of the elements of:

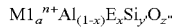

where M1 is at least one exchangeable cation selected from the group consisting of alkali metals, alkaline earth metals, rare earth metals, ammonium ion, hydrogen ion and mixtures thereof, a is the mole ratio of M1 to (Al+E) and varies from 0.05 to about 50, E is an element selected from the group consisting of gallium, iron, boron, chromium, indium and mixtures thereof, x is the mole fraction of E and varies from 0 to 1.0, n is the weighted average valence of M1 and has a value of about +1 to about +3, y' is the mole ratio of Si to (Al+E) and is greater than about 6.5 and z'' is the mole ratio of O to (Al+E) and has a value determined by the equation:

$$z''=(a \cdot n+3+4 \cdot y')/2$$

the zeolite characterized in that it has an x-ray diffraction pattern having at least the d-spacings and relative intensities set forth in Table B:

TABLE B

| 2-θ | d(Å) | I/I$_o$% |
|---|---|---|
| 6.90-7.40 | 12.8-11.94 | w-vs |
| 8.15-8.66 | 10.84-10.21 | m-vs |
| 14.10-14.70 | 6.28-6.02 | w-vs |
| 19.40-20.10 | 4.57-4.41 | w-s |
| 22.00-22.85 | 4.04-3.89 | m-vs |
| 24.65-25.40 | 3.61-3.50 | w-m |
| 25.70-26.50 | 3.46-3.36 | w-vs. |

2. The process of claim 1 wherein the alkylation process comprises monoalkylation of aromatic compounds where an alkylatable aromatic compound is reacted with an olefin under alkylation conditions to provide an alkylated compound.

3. The process of claim 2 where the aromatic compound is benzene, the olefin is propylene and the alkylated compound is cumene.

4. The process of claim 2 where the alkylatable aromatic compound is selected from the group consisting of benzene, naphthalene, anthracene, phenanthrene and substituted derivates thereof.

5. The process of claim 2 where the olefin contains from 2 up to about 30 carbon atoms.

6. The process of claim 2 where the aromatic compound is benzene, the olefin is ethylene and the alkylated compound is ethylbenzene.

7. The process of claim 1 where the zeolite is thermally stable up to a temperature of about 600° C.

8. The process of claim 1 where M1 is selected from the group consisting of lithium, sodium, cesium, potassium, strontium, barium, calcium, magnesium, lanthanum, hydrogen, ammonium ion and mixtures thereof.

* * * * *

UNITED STATES PATENT AND TRADEMARK OFFICE
CERTIFICATE OF CORRECTION

PATENT NO. : 7,638,667 B2  Page 1 of 1
APPLICATION NO. : 11/457184
DATED : December 29, 2009
INVENTOR(S) : Jan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 548 days.

Signed and Sealed this

Ninth Day of November, 2010

David J. Kappos
*Director of the United States Patent and Trademark Office*